(12) United States Patent
Otrembiak et al.

(10) Patent No.: US 10,932,846 B2
(45) Date of Patent: Mar. 2, 2021

(54) ARTICULATION SECTION FOR SHAFT ASSEMBLY OF SURGICAL INSTRUMENT

(71) Applicant: ETHICON LLC, Guaynabo, PR (US)

(72) Inventors: Candice Otrembiak, Loveland, OH (US); Chad P. Boudreaux, Cincinnati, OH (US); Barry C. Worrell, Centerville, OH (US); Nathan Cummings, Blue Ash, OH (US); Kris E. Kallenberger, Cincinnati, OH (US); Michael R. Lamping, Cincinnati, OH (US)

(73) Assignee: Ethicon LLC, Quaynabo, PR (US)

( * ) Notice: Subject to any disclaimer, the term of this patent is extended or adjusted under 35 U.S.C. 154(b) by 685 days.

(21) Appl. No.: 15/686,753

(22) Filed: Aug. 25, 2017

(65) Prior Publication Data

US 2019/0059984 A1    Feb. 28, 2019

(51) Int. Cl.
*A61B 18/14* (2006.01)
*A61B 17/29* (2006.01)
*A61B 17/3205* (2006.01)
*A61B 17/00* (2006.01)
*A61B 18/00* (2006.01)

(52) U.S. Cl.
CPC ......... *A61B 18/1445* (2013.01); *A61B 17/29* (2013.01); *A61B 17/3205* (2013.01); *A61B 2017/00309* (2013.01); *A61B 2017/00327* (2013.01); *A61B 2017/2905* (2013.01); *A61B 2017/2927* (2013.01); *A61B 2017/2929* (2013.01); *A61B 2018/0063* (2013.01);
(Continued)

(58) Field of Classification Search
CPC .............. A61B 18/085; A61B 18/1442; A61B 18/1445; A61B 2018/1455; A61B 2018/00172; A61B 2018/00607; A61B 2018/0063; A61B 2018/00619; A61B 2018/00184; A61B 17/29; A61B 2017/2905; A61B 2017/2908; A61B 2017/2927; A61B 2017/2929; A61B 2017/00309; A61B 2017/00314
USPC ...... 606/41, 46, 48, 50–52; 607/98, 99, 115, 607/116
See application file for complete search history.

(56) References Cited

U.S. PATENT DOCUMENTS 4,805,823 A    2/1989  Rothfuss
5,415,334 A    5/1995  Williamson, IV et al.
(Continued)

OTHER PUBLICATIONS

U.S. Appl. No. 61/410,603, entitled "Energy-Based Surgical Instruments," filed Nov. 5, 2010.
(Continued)

*Primary Examiner* — Thomas A Giuliani
(74) *Attorney, Agent, or Firm* — Frost Brown Todd LLC

(57) ABSTRACT

An apparatus includes a body, a shaft assembly, an end effector, and an articulation section. The articulation section is longitudinally interposed between a distal end of the shaft assembly and a proximal end of the end effector. The articulation section is configured to flex to thereby provide deflection of the end effector away from the longitudinal axis of the shaft assembly. The articulation section includes a first frame member, a second frame member, and a sleeve. The proximal end of the second frame member is proximal to the proximal end of the first frame member. The sleeve is disposed about the first and second frame members.

18 Claims, 30 Drawing Sheets

(52) U.S. Cl.
CPC ............ *A61B 2018/00601* (2013.01); *A61B 2018/00619* (2013.01); *A61B 2018/1455* (2013.01)

(56) References Cited

U.S. PATENT DOCUMENTS

| | | | |
|---|---|---|---|
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,500,176 B1 | 12/2002 | Truckai et al. | |
| 6,783,524 B2 | 8/2004 | Anderson | |
| 6,978,921 B2 | 12/2005 | Shelton, IV et al. | |
| 7,000,818 B2 | 2/2006 | Shelton, IV et al. | |
| 7,112,201 B2 | 9/2006 | Truckai et al. | |
| 7,125,409 B2 | 10/2006 | Truckai et al. | |
| 7,143,923 B2 | 12/2006 | Shelton, IV et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,303,108 B2 | 12/2007 | Shelton, IV | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,381,209 B2 | 6/2008 | Truckai et al. | |
| 7,434,715 B2 | 10/2008 | Shelton, IV et al. | |
| 7,721,930 B2 | 5/2010 | Mckenna et al. | |
| 9,492,224 B2 | 11/2016 | Boudreaux et al. | |
| 9,526,565 B2 | 12/2016 | Strobl | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0264193 A1 | 10/2010 | Huang et al. | |
| 2011/0015660 A1 | 1/2011 | Wiener et al. | |
| 2011/0087212 A1 | 4/2011 | Aldridge et al. | |
| 2011/0087218 A1 | 4/2011 | Boudreaux et al. | |
| 2012/0078243 A1* | 3/2012 | Worrell ............ A61B 17/07207 606/33 |
| 2012/0078247 A1 | 3/2012 | Worrell et al. | |
| 2012/0083783 A1 | 4/2012 | Davison et al. | |
| 2012/0116379 A1 | 5/2012 | Yates et al. | |
| 2012/0239012 A1 | 9/2012 | Laurent et al. | |
| 2013/0023868 A1 | 1/2013 | Worrell et al. | |
| 2013/0030428 A1 | 1/2013 | Worrell et al. | |
| 2013/0123783 A1* | 5/2013 | Marczyk ............ A61B 17/29 606/45 |
| 2014/0276931 A1* | 9/2014 | Parihar ............ A61B 34/30 606/130 |
| 2016/0100882 A1 | 4/2016 | Boudreaux et al. | |
| 2016/0270839 A1* | 9/2016 | Stewart ............ A61B 18/1482 |
| 2016/0303403 A1 | 10/2016 | Shapiro et al. | |
| 2018/0021051 A1 | 1/2018 | Worrell et al. | |

OTHER PUBLICATIONS

International Search Report and Written Opinion dated Feb. 11, 2019 for International Application No. PCT/US2018/047309, 20 pages.

International Preliminary Report on Patentability dated Feb. 25, 2020 for International Application No. PCT/US2018/047309, 12 pages.

\* cited by examiner

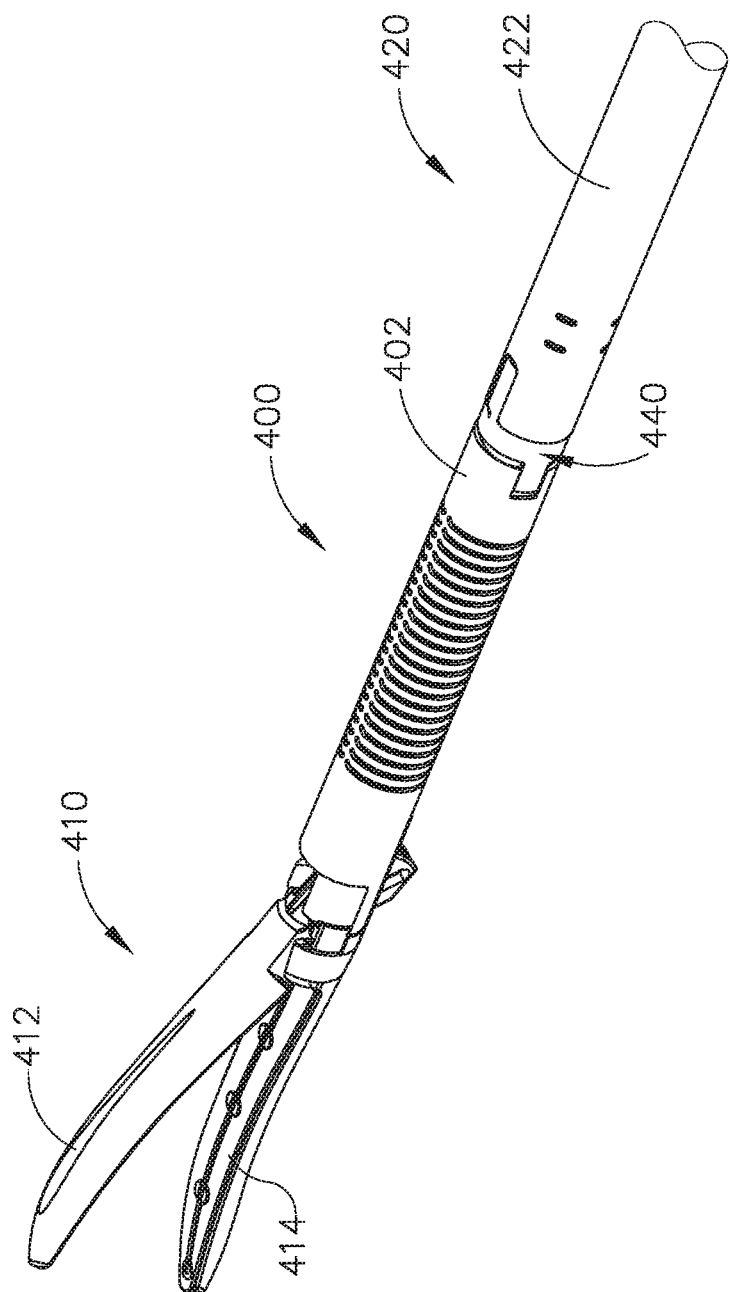

ARTICULATION SECTION FOR SHAFT ASSEMBLY OF SURGICAL INSTRUMENT

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0083783, entitled "Surgical Instrument with Jaw Member," published Apr. 5, 2012, issued as U.S. Pat. No. 8,888,809 on Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pub. No. 2012/0078247, entitled "Articulation Joint Features for Articulating Surgical Device," published Mar. 29, 2012, issued as U.S. Pat. No. 9,402,682 on Aug. 2, 2016 the disclosure of which is incorporated by reference herein; U.S. Pub. No. 2013/0030428, entitled "Surgical Instrument with Multi-Phase Trigger Bias," published Jan. 31, 2013, issued as U.S. Pat. No. 9,089,327 on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, issued as U.S. Pat. No. 9,545,253 on Jan. 17, 2017, the disclosure of which is incorporated by reference herein.

Still other examples of electrosurgical cutting instruments and related concepts are disclosed in U.S. Pat. No. 9,526,565, entitled "Electrosurgical Devices," issued. Dec. 27, 2016, the disclosure of which is incorporated by reference herein; U.S. Pat. No. 9,492,224, entitled "Multi-Function Bi-Polar Forceps," issued Nov. 15, 2016, the disclosure of which is incorporated by reference herein; and U.S. Pub. No. 2016/0100882, entitled "Methods and Devices for Articulating Laparoscopic Energy Device," published Apr. 14, 2016, issued as U.S. Pat. No. 10,292,758 on May 21, 2019, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11 depicts a perspective view of an exemplary alternative articulation assembly that may be incorporated into the instrument of FIG. 1;

Figure 1:
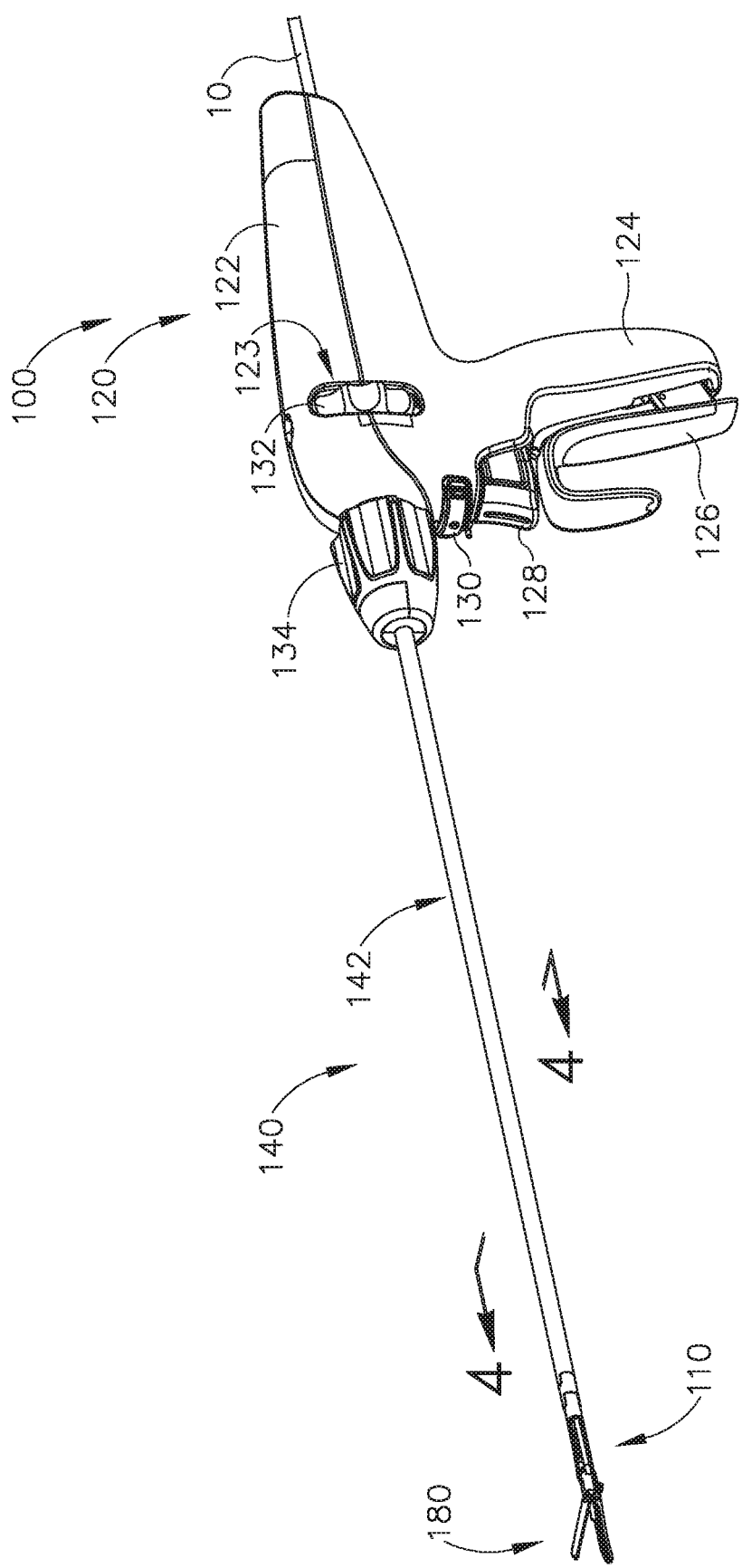
FIG. 1 depicts a perspective view of an exemplary electrosurgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Instrument

FIGS. 1-10 show an exemplary electrosurgical instrument (100). As best seen in FIG. 1, electrosurgical instrument (100) includes a handle assembly (120), a shaft assembly (140), an articulation assembly (110), and an end effector (180). As will be described in greater detail below, end effector (180) of electrosurgical instrument (100) is operable to grasp, cut, and seal or weld tissue (e.g., a blood vessel, etc.). In this example, end effector (180) is configured to seal or weld tissue by applying bipolar radio frequency (RF) energy to tissue. However, it should be understood electrosurgical instrument (100) may be configured to seal or weld tissue through any other suitable means that would be apparent to one having ordinary skill in the art in view of the teachings herein. For example, electrosurgical instrument (100) may be configured to seal or weld tissue via an ultrasonic blade, staples, etc. In the present example, electrosurgical instrument (100) is electrically coupled to a power source (not shown) via power cable (10).

The power source may be configured to provide all or some of the electrical power requirements for use of electrosurgical instrument (100). Any suitable power source may be used as would be apparent to one having ordinary skill in the art in view of the teachings herein. By way of example only, the power source may comprise a GEN04 or GEN11 sold by Ethicon Endo-Surgery, Inc. of Cincinnati, Ohio. In addition, or in the alternative, the power source may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. While in the current example, electrosurgical instrument (100) is coupled to a power spruce via power cable (10), electrosurgical instrument (100) may contain an internal power source or plurality of power sources, such as a battery and/or supercapacitors, to electrically power electrosurgical instrument (100). Of course, any suitable combination of power sources may be utilized to power electrosurgical instrument (100) as would be apparent to one having ordinary skill in the art in view of the teaching herein Handle assembly (120) is configured to be grasped by an operator one hand, such that an operator may control and manipulate electrosurgical instrument (100) with a single hand. Shaft assembly (140) extends distally from handle assembly (120) and connects to articulation assembly (110). Articulation assembly (110) is also connected to a proximal end of end effector (180). As will be described in greater detail below, components of handle assembly (120) are configured to control end effector (180) such that an operator may grasp, cut, and seal or weld tissue. As will also be described in greater detail below, articulation assembly (110) is configured to deflect end effector (180) from the longitudinal axis defined by shaft assembly (140).

Handle assembly (120) includes a body (122), a pistol grip (124), a jaw closure trigger (126), a knife trigger (128), an activation button (130), an articulation control (132), and a knob (134). As will be described in greater detail below, jaw closure trigger (126) may be pivoted toward and away from pistol grip (124) and/or body (122) to open and close jaws (182, 184) of end effector (180) to grasp tissue. Knife trigger (128) may be pivoted toward and away from pistol grip (124) and/or body (122) to actuate a knife member (360) within the confines of jaws (182, 184) to cut tissue captured between jaws (182, 184). Activation button (130) may be pressed to apply radio frequency (RF) energy to tissue via electrode surfaces (194, 196) of jaws (182, 184), respectively.

Body (122) of handle assembly (120) defines an opening (123) in which a portion of articulation control (132) protrudes from. Articulation control (132) is rotatably disposed within body (122) such that an operator may rotate the portion of articulation control (132) protruding from opening (123) to rotate the portion of articulation control (132) located within body (122). As will be described in greater detail below, rotation of articulation control (132) relative to body (122) will drive deflection of end effector (180) from the longitudinal axis defined by shaft assembly (140).

Knob (134) is rotatably disposed on the distal end of body (122) and configured to rotate end effector (180), articulation assembly (110), and shaft assembly (140) about the longitudinal axis of shaft assembly (140) relative to handle assembly (120). While in the current example, end effector (180), articulation assembly (110), and shaft assembly (140) are rotated by knob (134), knob (134) may be configured to rotate end effector (180) and articulation assembly (110) relative to selected portions of shaft assembly (140). Knob (134) may include any suitable features to rotate end effector (180), articulation assembly (110), and shaft assembly (140) as would be apparent to one having ordinary skill in the art in view of the teachings herein.

Figure 4:
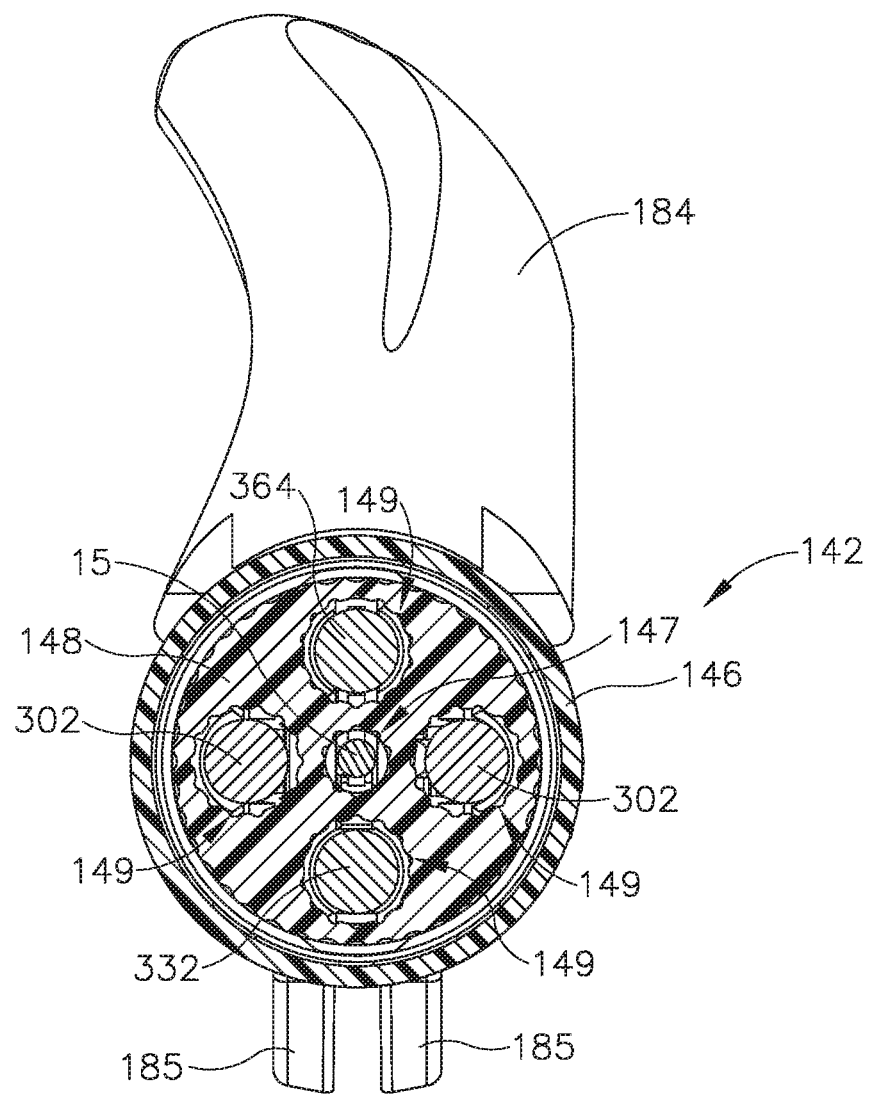
FIG. 4 depicts a cross-sectional rear view of a shaft assembly of the instrument of FIG. 1, taken along line 4-4 of FIG. 1.
Figure 7A:
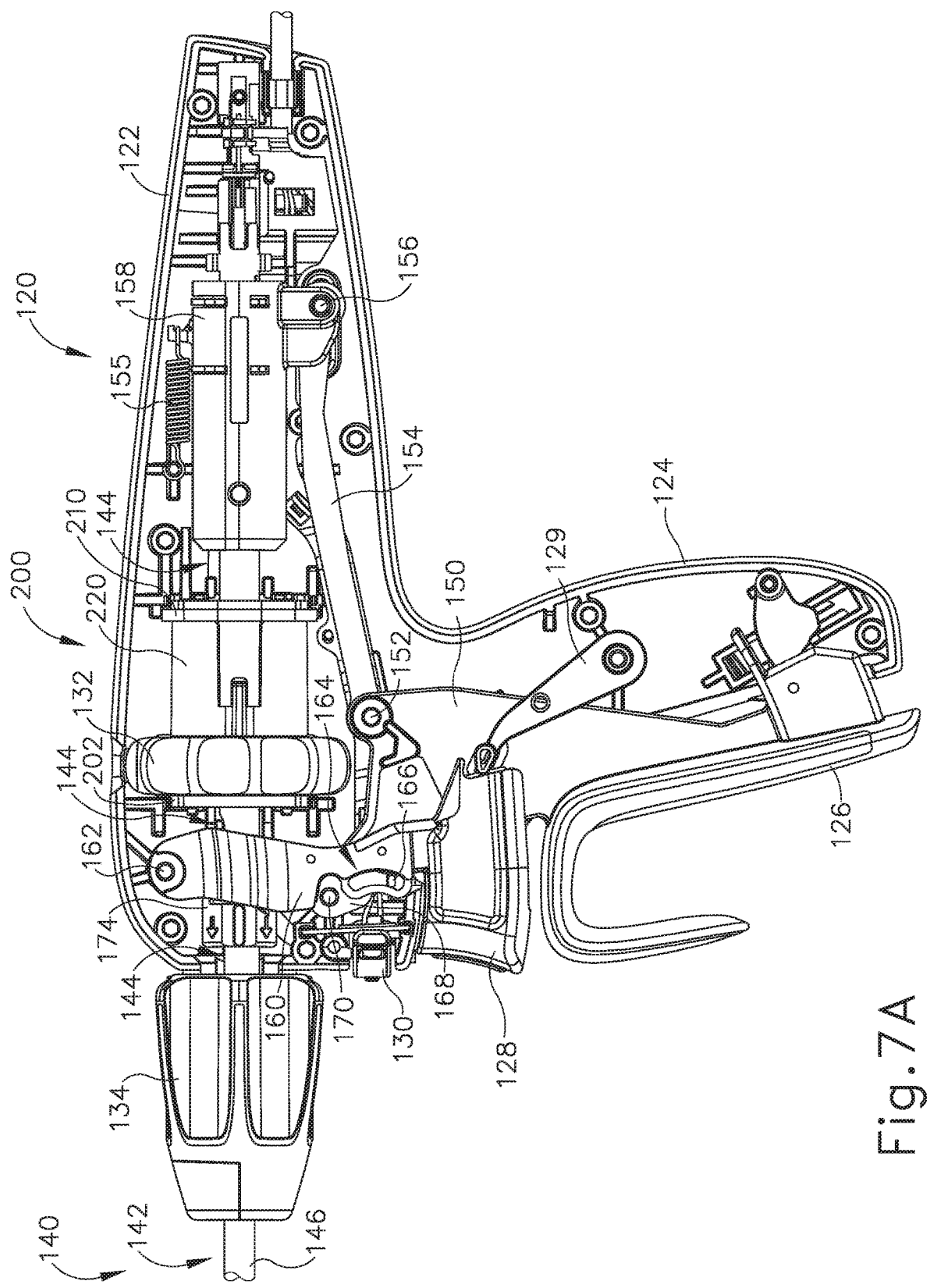
FIG. 7A depicts a side elevational view of a handle assembly of the instrument of FIG. 1, where the end effector is in an open and unfired state, where a portion of the handle assembly is omitted for purposes of clarity.
Figure 7B:
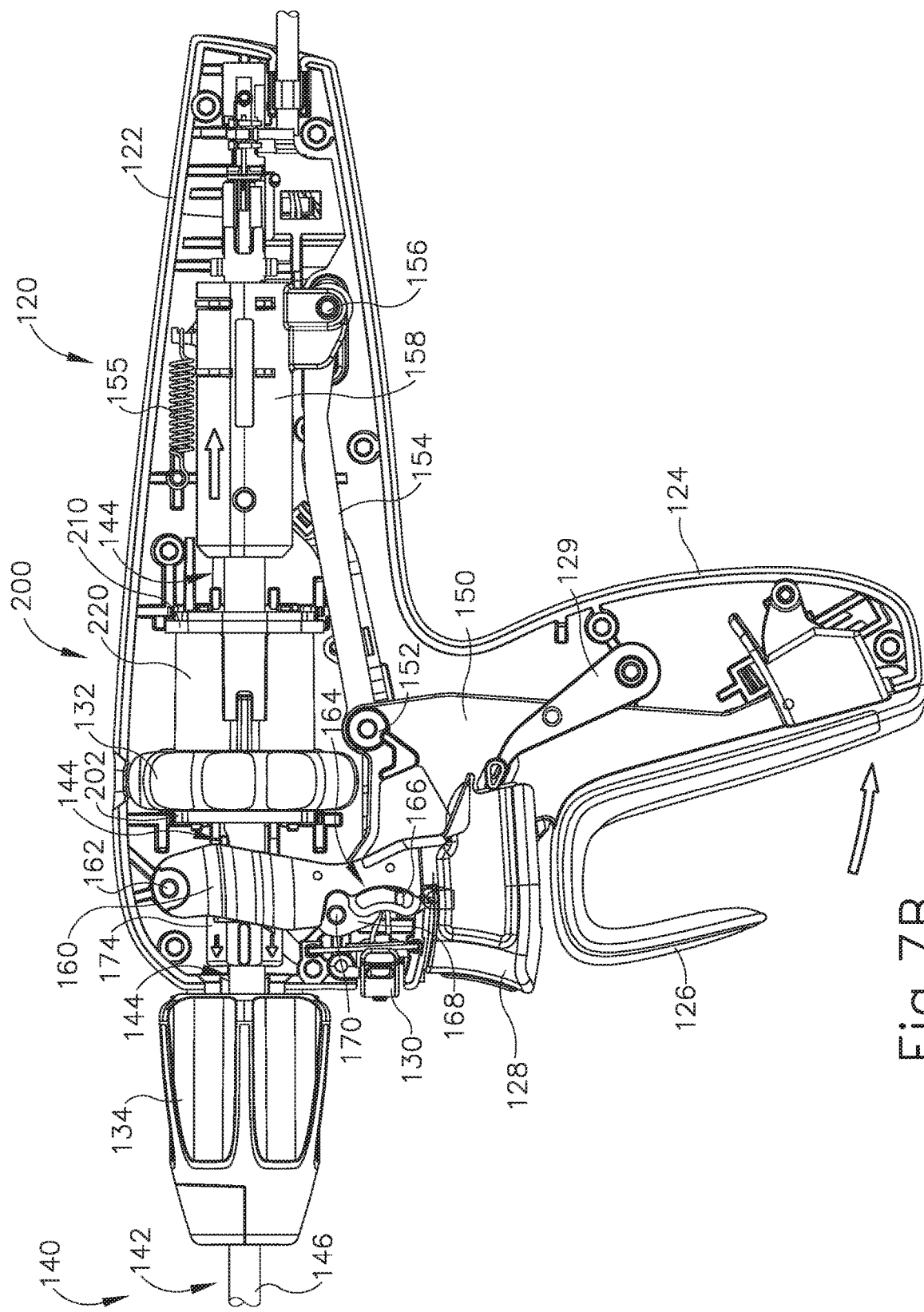
FIG. 7B depicts a side elevational view of the handle assembly of FIG. 7A, where the end effector is in a closed and unfired state, where a portion of the handle assembly is omitted for purposes of clarity.
Figure 7C:
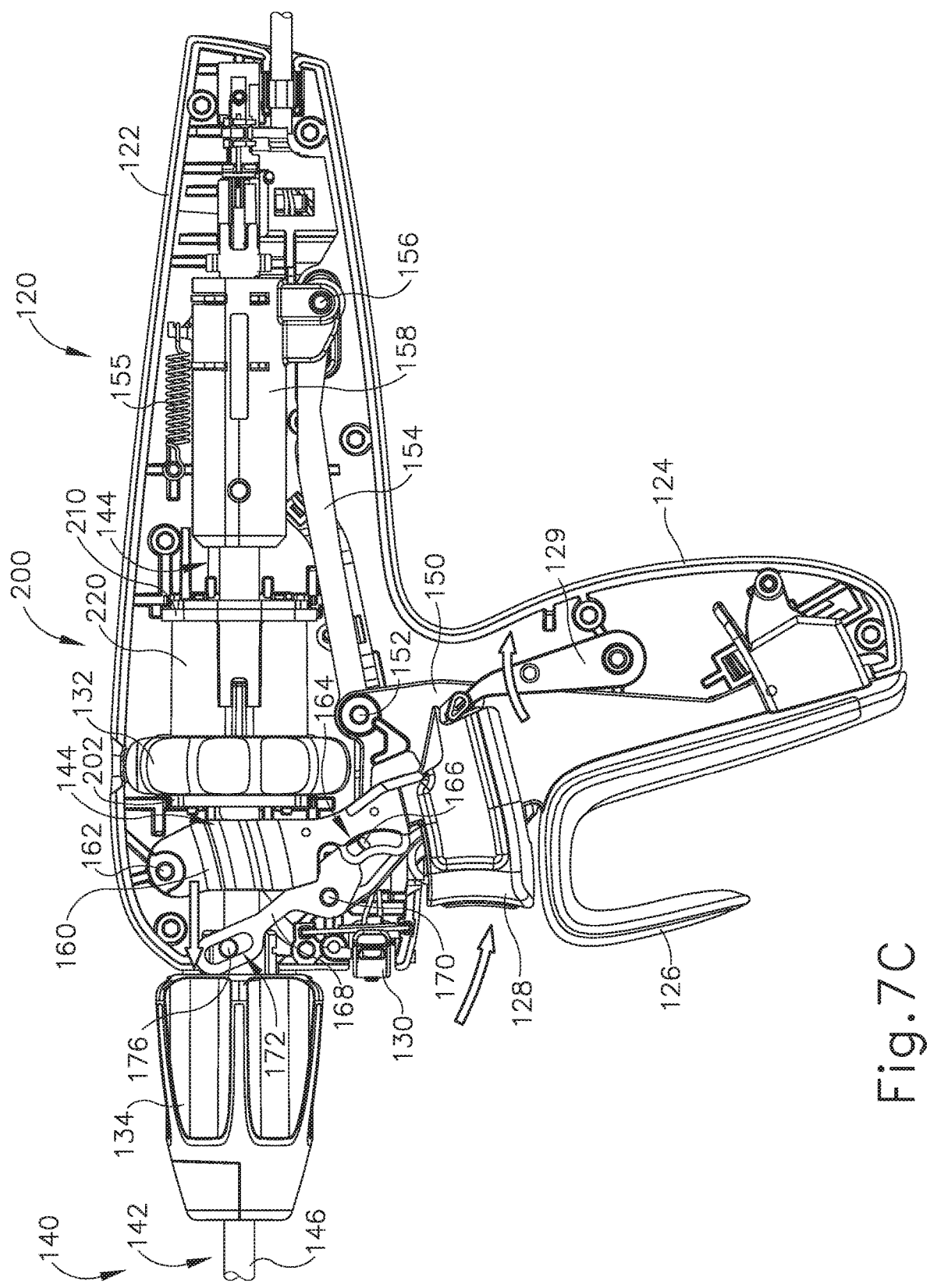
FIG. 7C depicts a side elevational view of the handle assembly of FIG. 7A, where the end effector is in a closed and fired state, where a portion of the handle assembly is omitted for purposes of clarity.

As best seen in FIGS. 7A-7C, shaft assembly (140) includes distal portion (142) extending distally from handle assembly (120), and a proximal portion (144) housed within the confines of body (122) of handle assembly (120). As seen in FIG. 4, distal portion (142) of shaft assembly (140) includes an external sheath (146) and a housing member (148) disposed within external sheath (146). Housing member (148) defines four longitudinal pathways (149) disposed around a central longitudinal pathway (147). Longitudinal pathways (149) slidably house two rod portions (302) of two articulation connectors (300), a rod portion (332) of jaw closure connector (330), and a knife rod (364) of knife member (360); while central longitudinal pathway (147) houses electrical wire (15). As will be described in greater detail below, articulation connectors (300) are configured to couple certain actuating portions of handle assembly (120) with end effector (180). Articulation connectors (300) are configured to translate relative to shaft assembly (140) to drive articulation of end effector (180) relative to the longitudinal axis defined by shaft assembly (140). As will also be described in greater detail below, jaw closure connector (330) is configured to couple an actuating portion of handle assembly (120) with end effector (180). Jaw closure connector (330) is configured to translate relative to shaft assembly (140) to open and close jaws (182, 184) of end effector (180). As will also be described in greater detail below, knife member (360) is configured to couple to an actuating portion of handle assembly (120) to translate a distal cutting edge (362) within the confines of end effector (180).

Figure 9A:
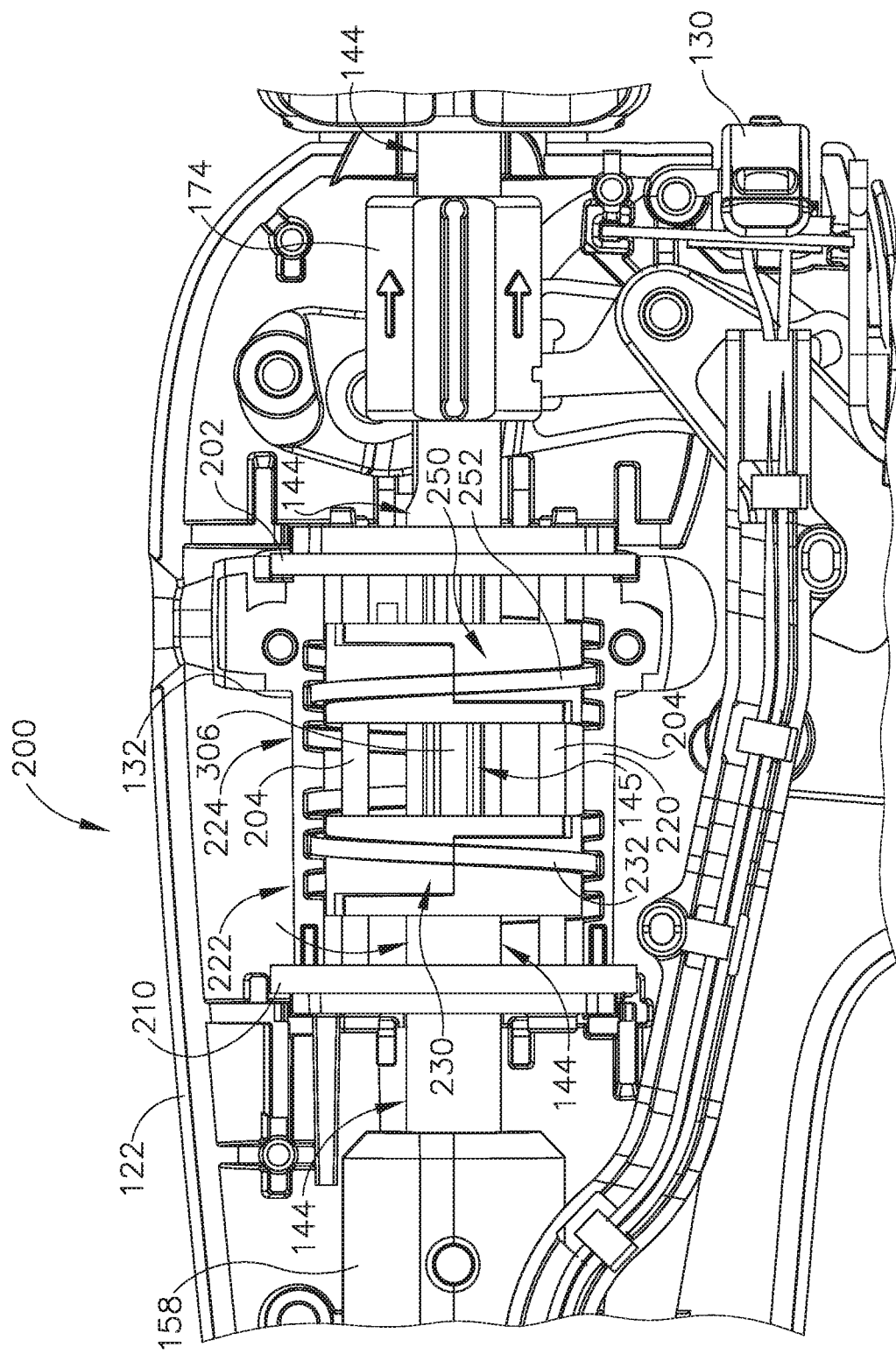
FIG. 9A depicts an elevational side view of the handle assembly of FIG. 7A, where the articulation assembly of FIG. 2 is a non-articulated configuration, where selected portions of the handle assembly are omitted for purposes of clarity.
Figure 9B:
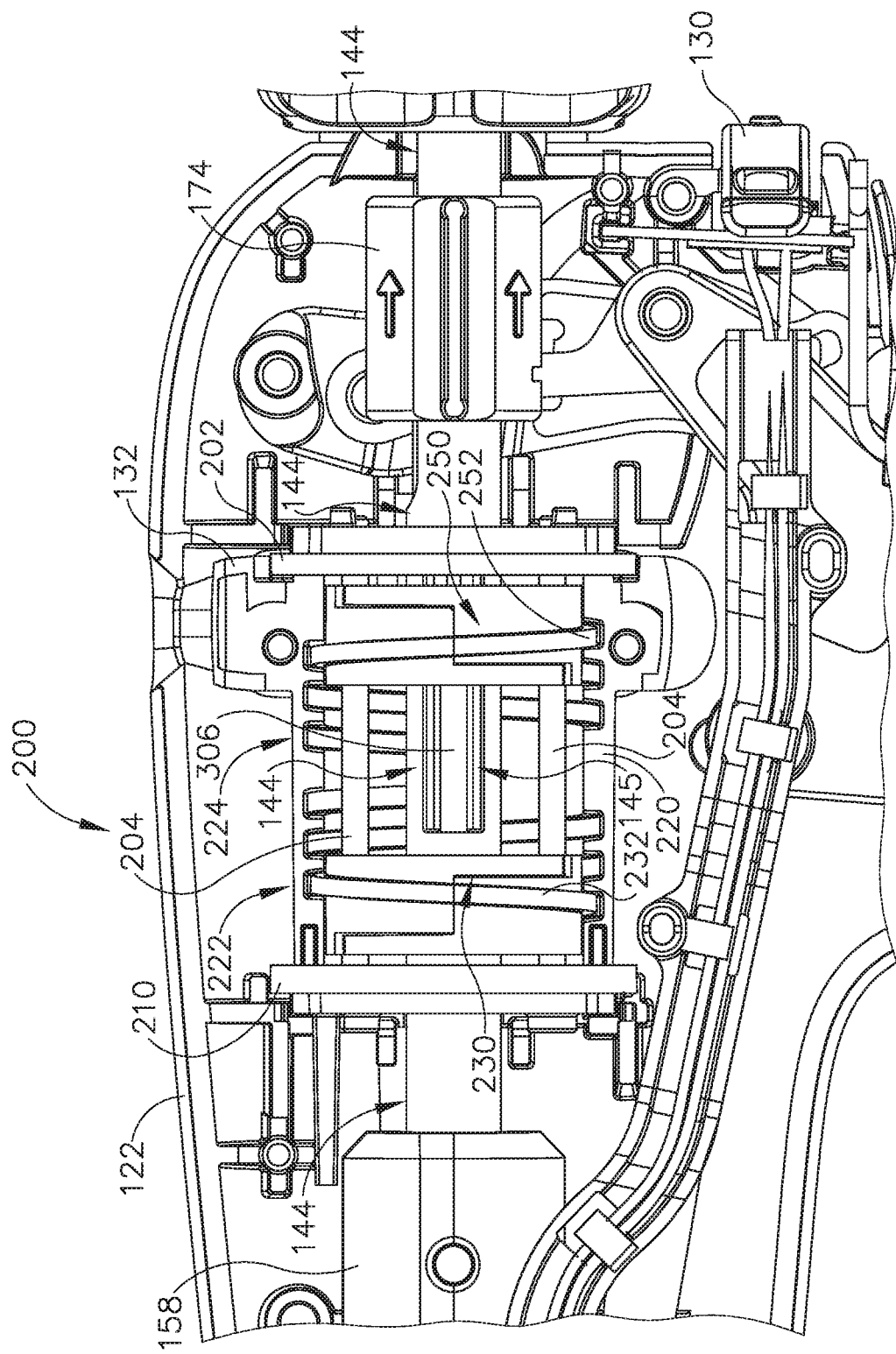
FIG. 9B depicts an elevational side view of the handle assembly of FIG. 7A, where the articulation assembly of FIG. 2 is in a first articulated configuration, were selected portions of the handle assembly are omitted for purposes of clarity.
Figure 9C:
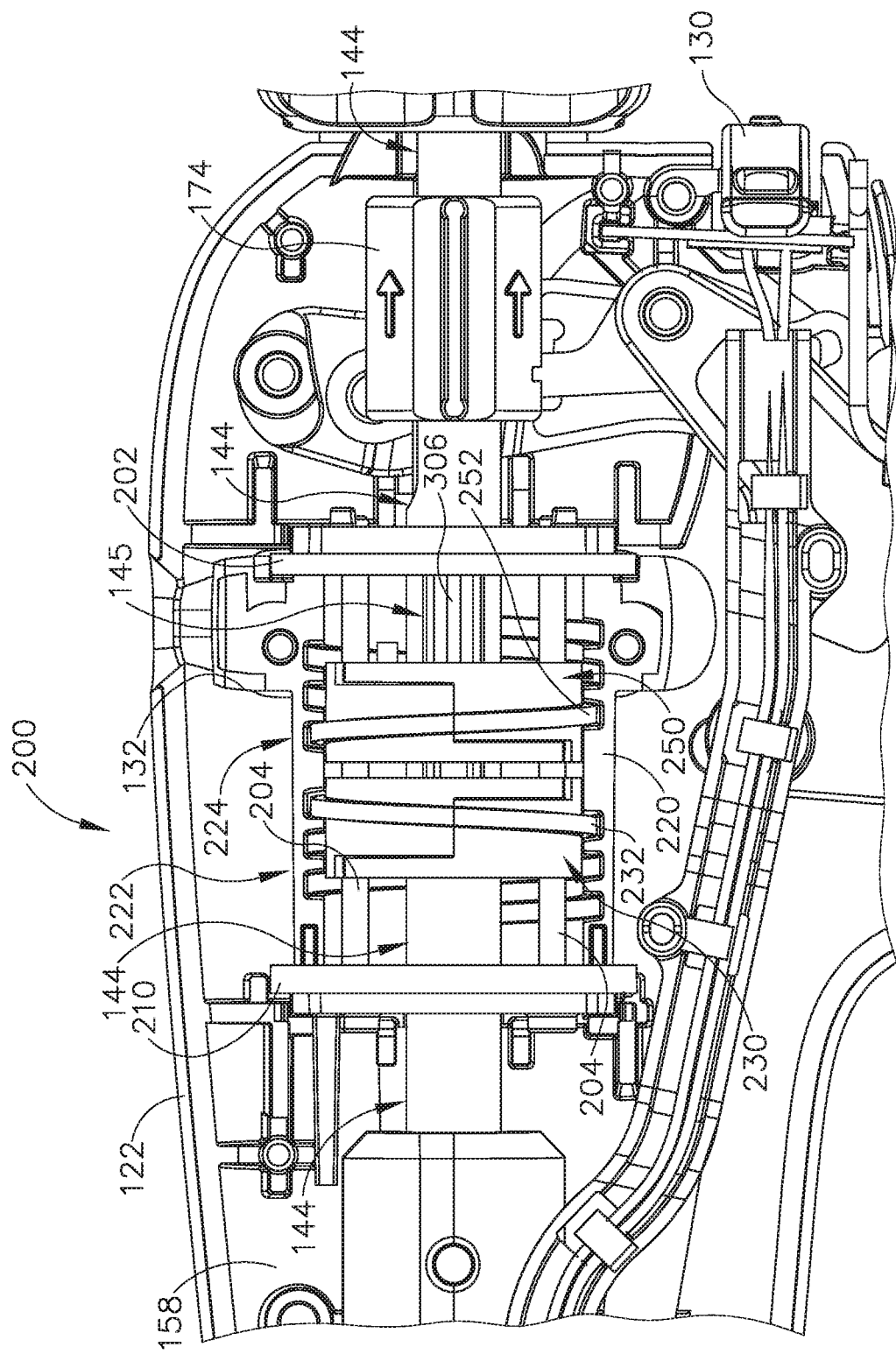
FIG. 9C depicts an elevational side view of the handle assembly of FIG. 7A, where the articulation assembly of FIG. 2 is in a second articulated configuration, were selected portions of the handle assembly are omitted for purposes of clarity.

As will be described in greater detail below, proximal portion (144) of shaft assembly (140) extends within handle assembly (120) and through certain actuating portions of handle assembly (120) that are configured to longitudinally drive rod portions (302, 332, 364). As will also be described in greater detail below, rod portions (302, 332, 364) extend within proximal portion (144) and couple with correspond actuating portions of handle assembly (120). As best shown in FIGS. 9A-9C, proximal portion (144) defines slots (145) to allow actuating portions of handle assembly (120) to couple with rod portions (302, 332, 364) such that translation of actuation portions of handle assembly (120) relative to shaft assembly (140) longitudinally drives rod portions (302, 332, 364) relative to shaft assembly (140). Rod portions (302, 332, 364) are coupled to certain actuating portions of handle assembly (120) such that rod portions (302, 332, 364) may rotate with shaft assembly (140) relative to actuating portions of handle assembly (120); but also such that rod portions (302, 332, 364) longitudinally translate with actuating portions of handle assembly (120) relative to shaft assembly (140). In other words, an operator may utilize knob (134) to rotate shaft assembly (140) and rod portions (302, 332, 364) relative to handle assembly (120); but also may actuate rod portions (302, 332, 364) longitudinally relative to shaft assembly (140).

Figure 2:
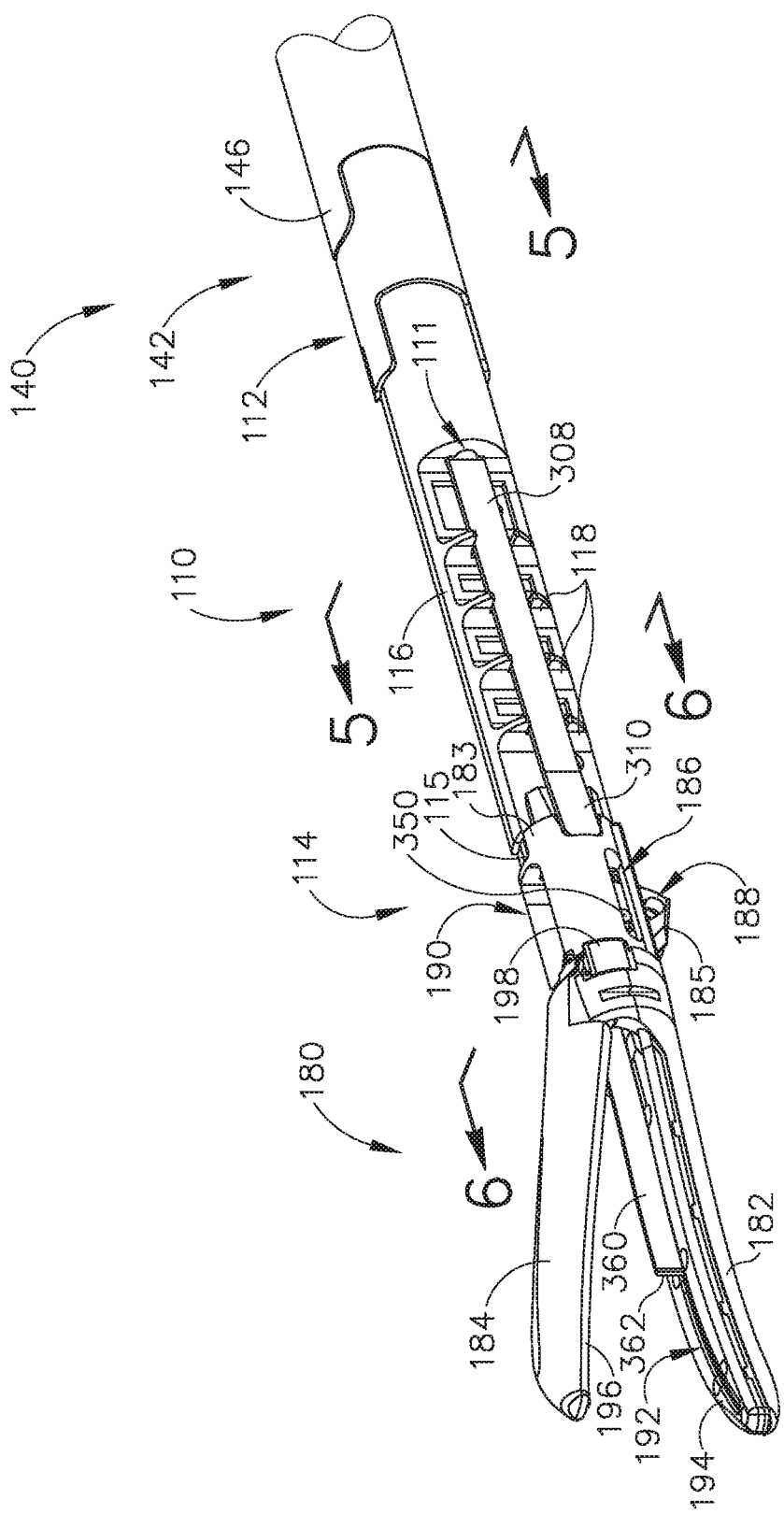
FIG. 2 depicts a perspective view of an exemplary articulation assembly and end effector of the instrument of FIG. 1.
Figure 3:
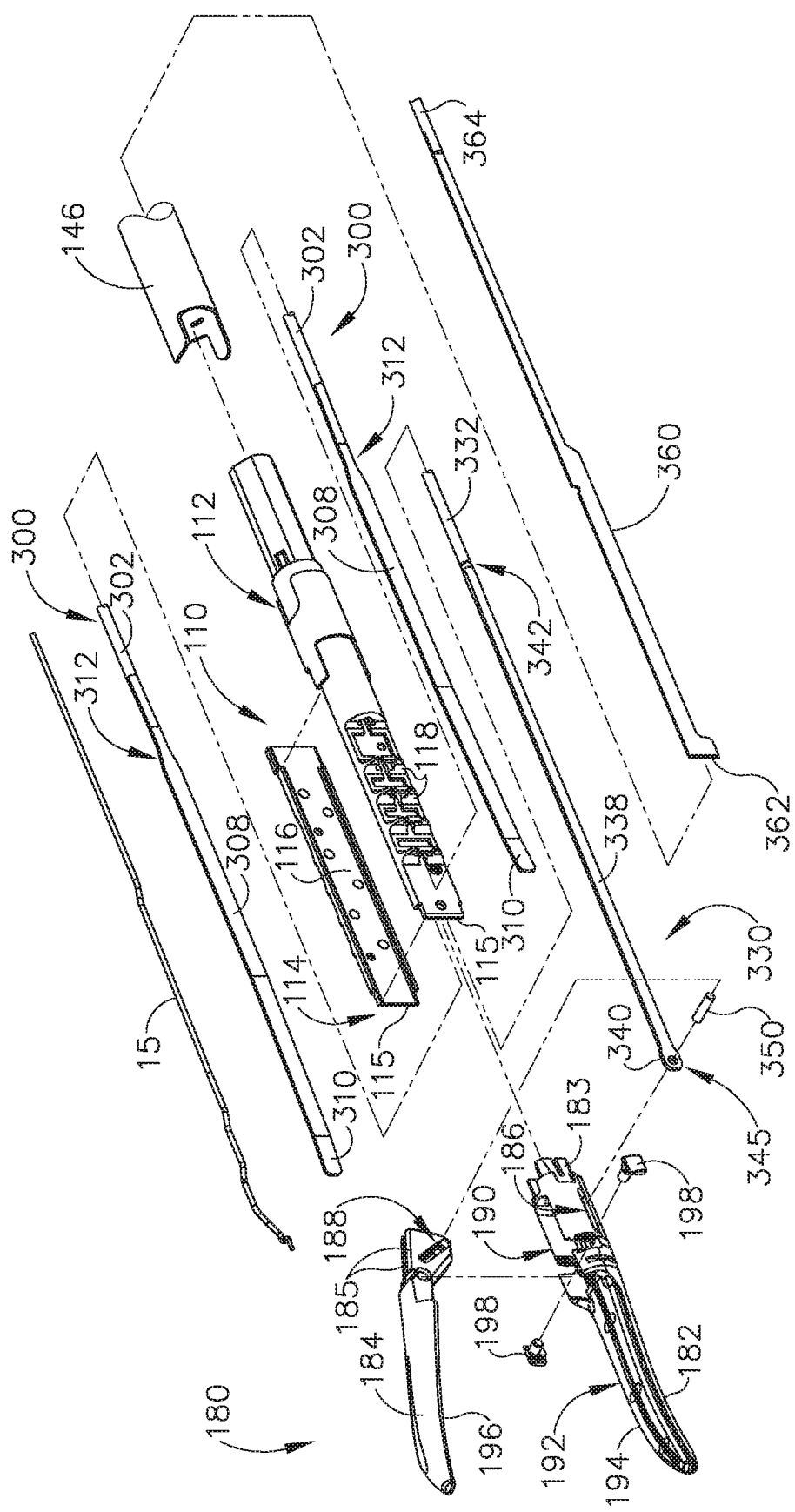
FIG. 3 depicts an exploded view of the articulation assembly and end effector of FIG. 2.
Figure 6:
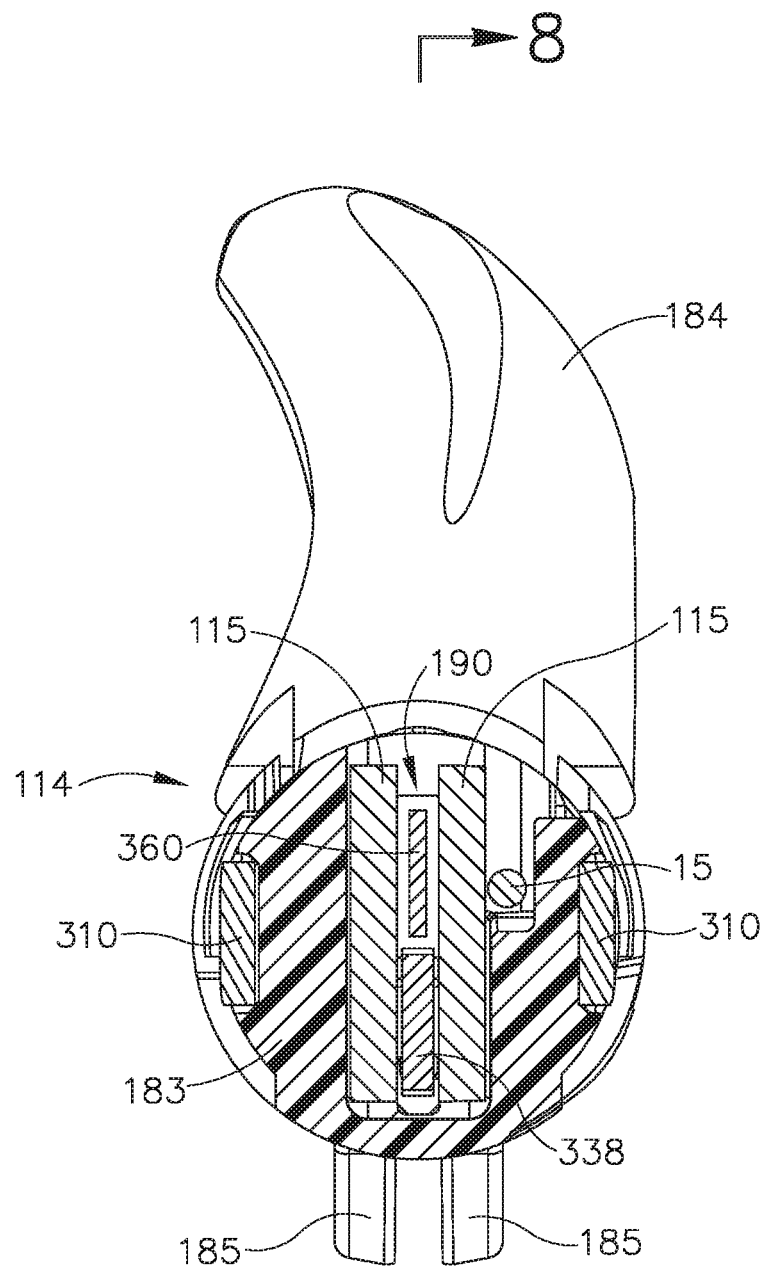
FIG. 6 depicts a cross-sectional rear view of the end effector of FIG. 2, taken along line 6-6 of FIG. 2.

FIGS. 2-3 show end effector (180), articulation assembly (110), and a distal portion (142) of shaft assembly (140). Articulation assembly (110) extends from a rigid proximal portion (112) to a distal portion (114). Rigid proximal portion (112) is fixed to outer sheath (146) of distal portion (142) of shaft assembly (140). As best seen in FIG. 6, distal portion (114) of articulation assembly (110) includes distal projections (115) inserted within the confines of proximal body (183) of lower jaw (182). A flexible member (116) extends from the distal end of rigid proximal portion (112) toward distal portion (114). As seen in FIG. 3, in the present example, two flexible members (116) are laterally coupled with each other such that both flexible members (116) extend along the same longitudinal axis. However, any other suitable combination or assembly of flexible members (116) may be used as would be apparent to one having ordinary skill in the art in view of the teachings herein.

Figure 10A:
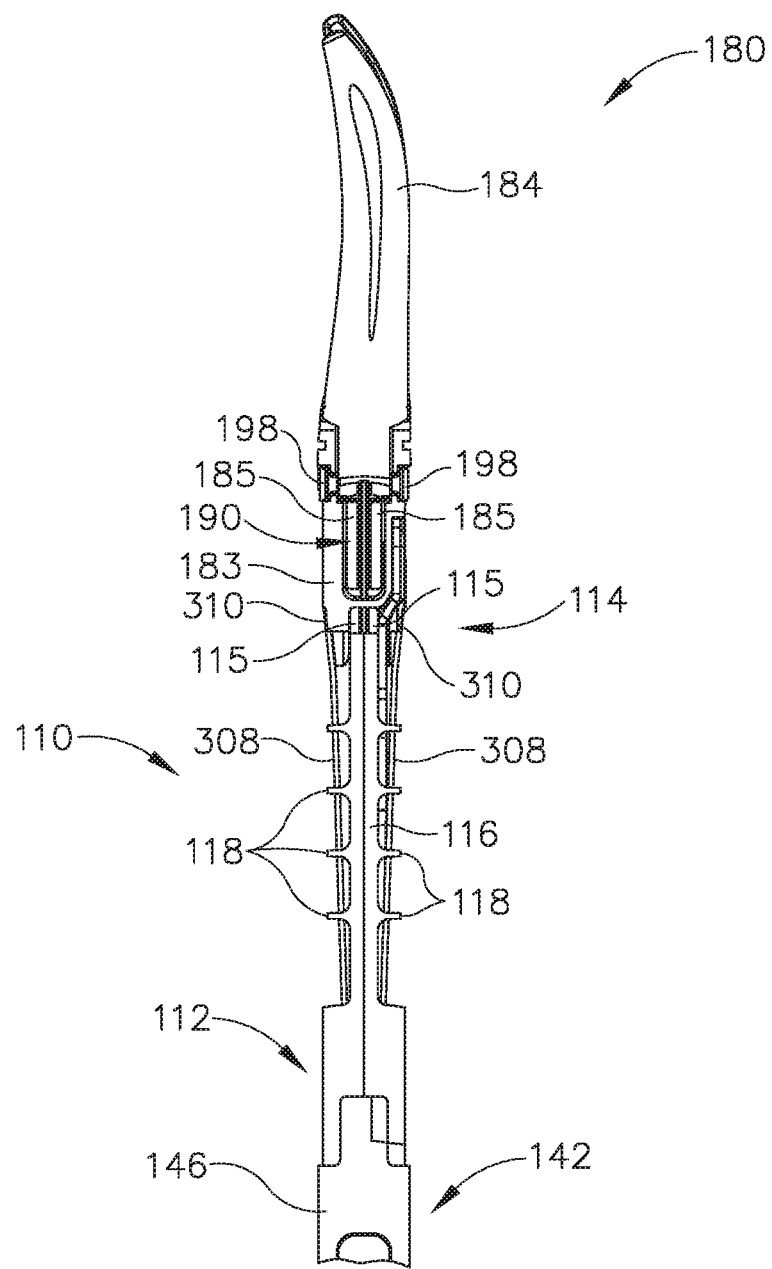
FIG. 10A depicts a top plan view of the end effector and articulation assembly of FIG. 2, where the articulation assembly is in the non-articulated configuration.
Figure 10B:
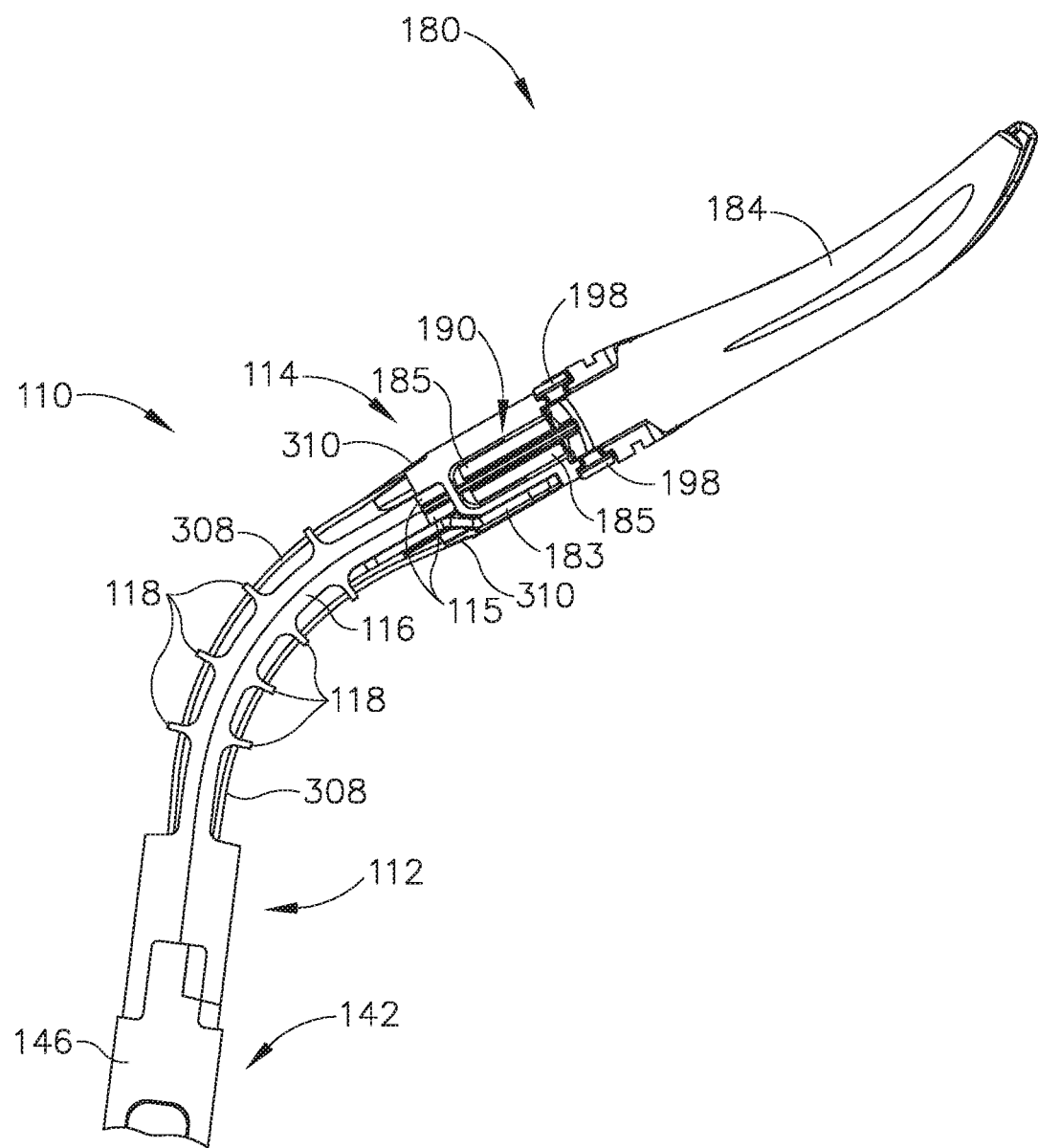
FIG. 10B depicts a top plan view of the end effector and articulation assembly of FIG. 2, where the articulation assembly is in the first articulated configuration.
Figure 10C:
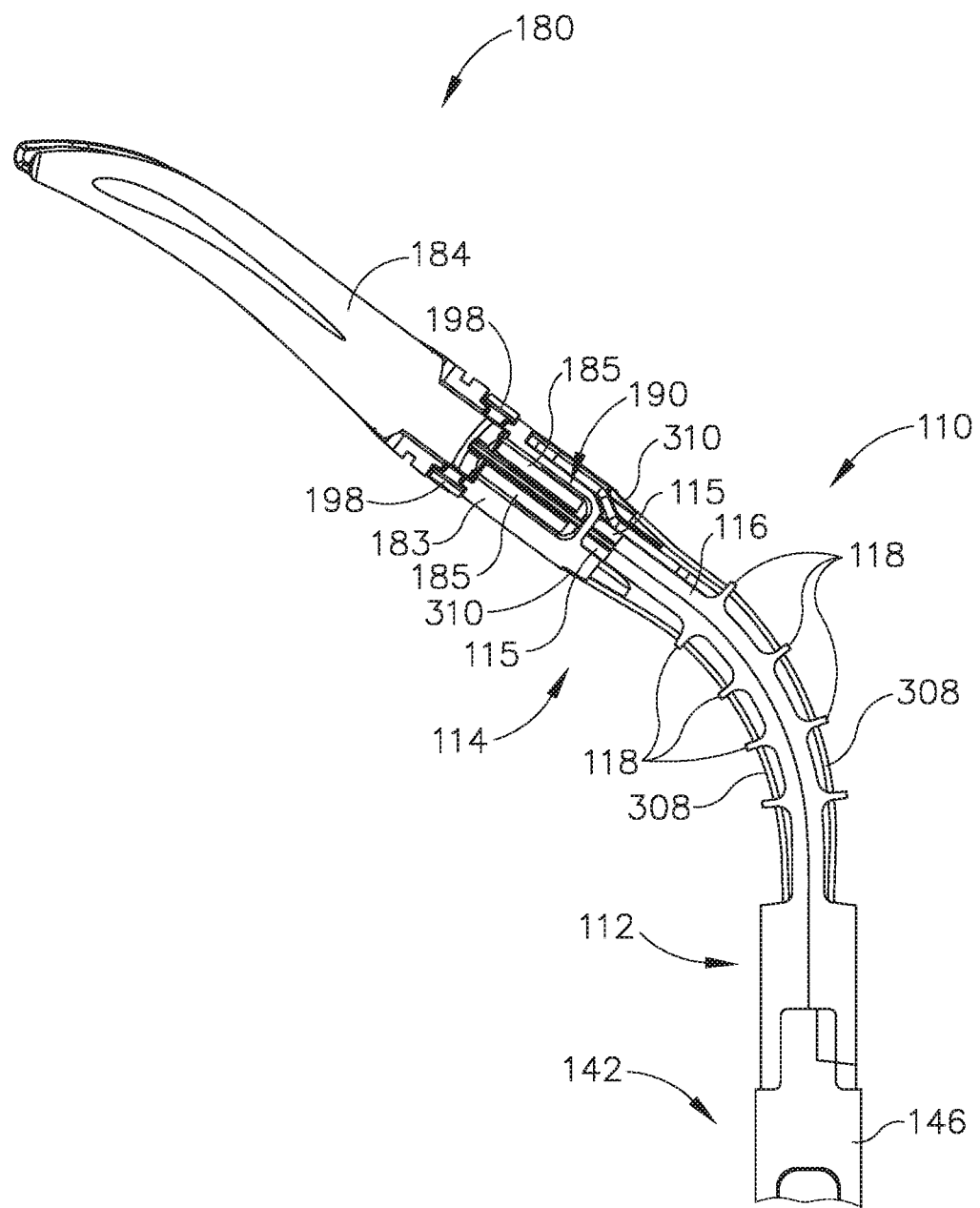
FIG. 10C depicts a top plan view of the end effector and articulation assembly of FIG. 2, where the articulation assembly is in the second articulated configuration.

Flexible members (116) include a plurality of guide members (118) that are configured to slidingly receive a band portion (308) of articulation connector (300). Flexible members (116) and band portions (308) are sufficiently flexible to bend relative to the longitudinal axis defined by shaft assembly (140) (as shown in FIGS. 10B-10C). As best seen in FIGS. 2 and 6, distal coupling portion (310) of articulation connector (300) is fixed to proximal body (183) of a lower jaw (182). As will be described in greater detail below, translation of articulation connectors (300) will drive deflection of end effector (180) relative to the longitudinal axis defined by shaft assembly (140).

Figure 5:
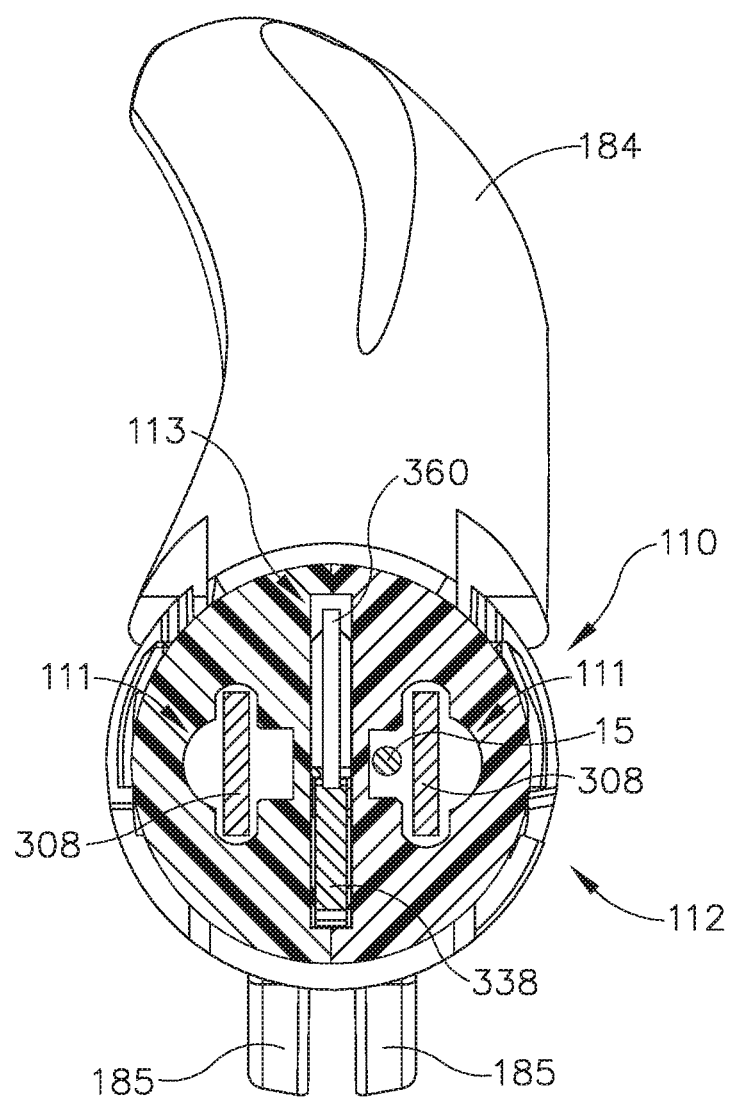
FIG. 5 depicts a cross-sectional rear view of the articulation assembly of FIG. 2, taken along line 5-5 of FIG. 2.

As shown in FIG. 5, rigid proximal portion (112) of articulation assembly (110) defines a pair of laterally offset pathways (111) and a central pathway (113). Laterally offset pathways (111) are dimensioned to slidably house corresponding band portions (308) of articulation connector (300) and electrical wire (15); while central pathway (113) is dimensioned to slidably house corresponding portions of knife member (360) and band portion (338) of jaw closure connector (330). Central pathway (313) extends through flexible member (316) and proximal portion (314) to provide a pathway for knife member (360) and band portion (338) of jaw closure connector (330) from shaft assembly (140) to end effector (180). Therefore, knife member (360) and band portion (338) of jaw closure connector (330) are both sufficiently flexible to bend relative to the longitudinal axis defined by shaft assembly (140) (as shown in FIGS. 11.0B-10C).

As best seen in FIGS. 2-3 and 8A-8C, end effector (180) includes lower jaw (182) pivotally coupled with an upper jaw (184) via pivot couplings (198). Lower jaw (182) includes a proximal body (183) defining a slot (186), while upper jaw (184) includes proximal arms (185) defining a slot (188). Lower jaw (182) also defines a central channel (190) that is configured to receive proximal arms (185) of upper jaw (184), portions of knife member (360), band portion (338) of jaw closure connecter (330), and pin (350). Slots (186, 188) each slidably receive pin (350), which is attached to a distal coupling portion (340) of jaw closure connector (330). As will be described in greater detail below, jaw closure connector (330) is operable to translate within central channel (190) of lower jaw (182). Translation of jaw closure connector (330) drives pin (350). As will be described in greater detail below, because pin (350) is located within both slots (186, 188) and slots (186, 188) are angled relative to each other, pin (350) cams against proximal arms (185) to pivot upper jaw (184) toward and away from lower jaw (182) about pivot couplings (198). Therefore, upper jaw (184) is configured to pivot toward and away from lower jaw (182) about pivot couplings (198) to grasp tissue.

The term "pivot" does not necessarily require rotation about a fixed axis, but may include rotation about an axis that moves relative to end effector (180). Therefore, the axis at which upper jaw (184) pivots about lower jaw (182) may translate relative to both upper jaw (184) and lower jaw (182). Any suitable translation of the pivot axis may be used as would be apparent to one having ordinary skill in the art in view of the teachings herein.

Figure 8A:
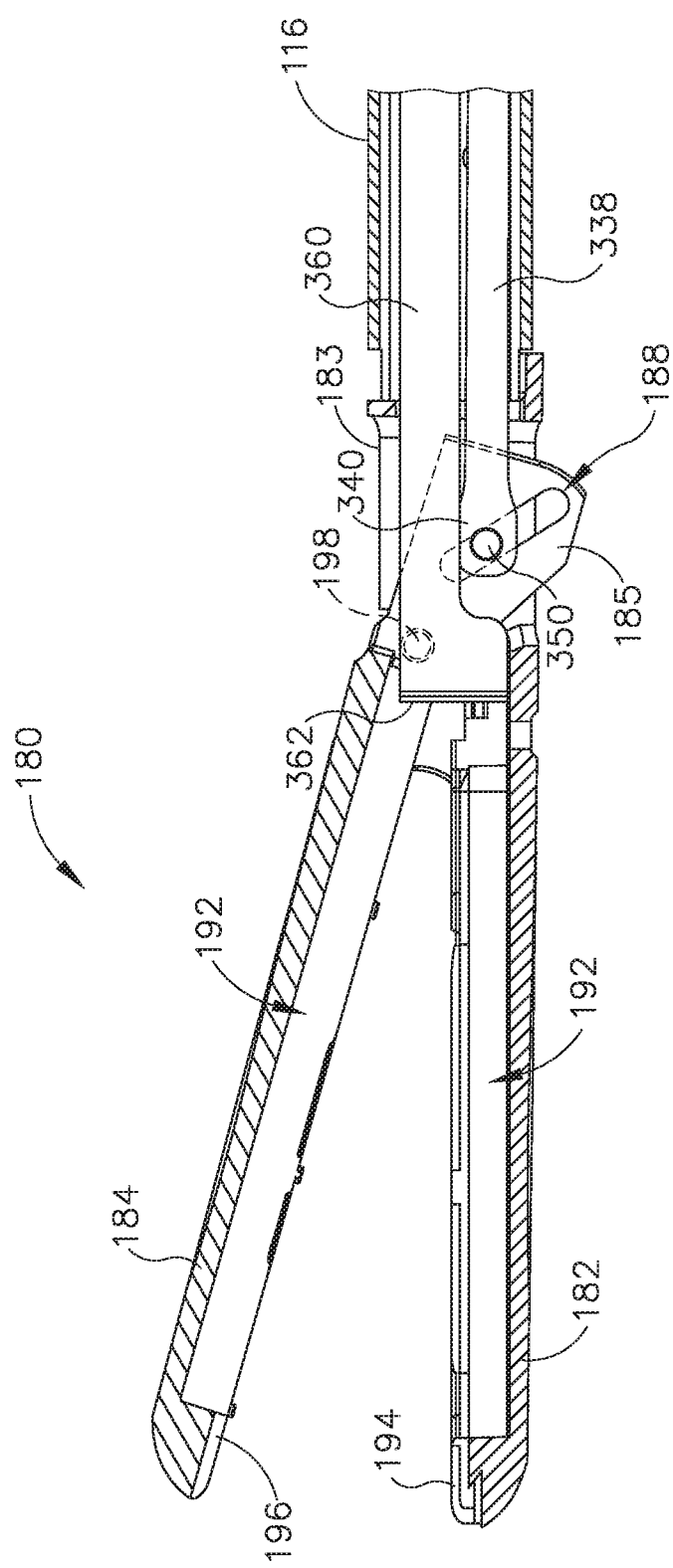
FIG. 8A depicts a cross-sectional side view of the end effector of FIG. 2, where the end effector is in the open and unfired state, taken along line 8-8 of FIG. 6.
Figure 8B:
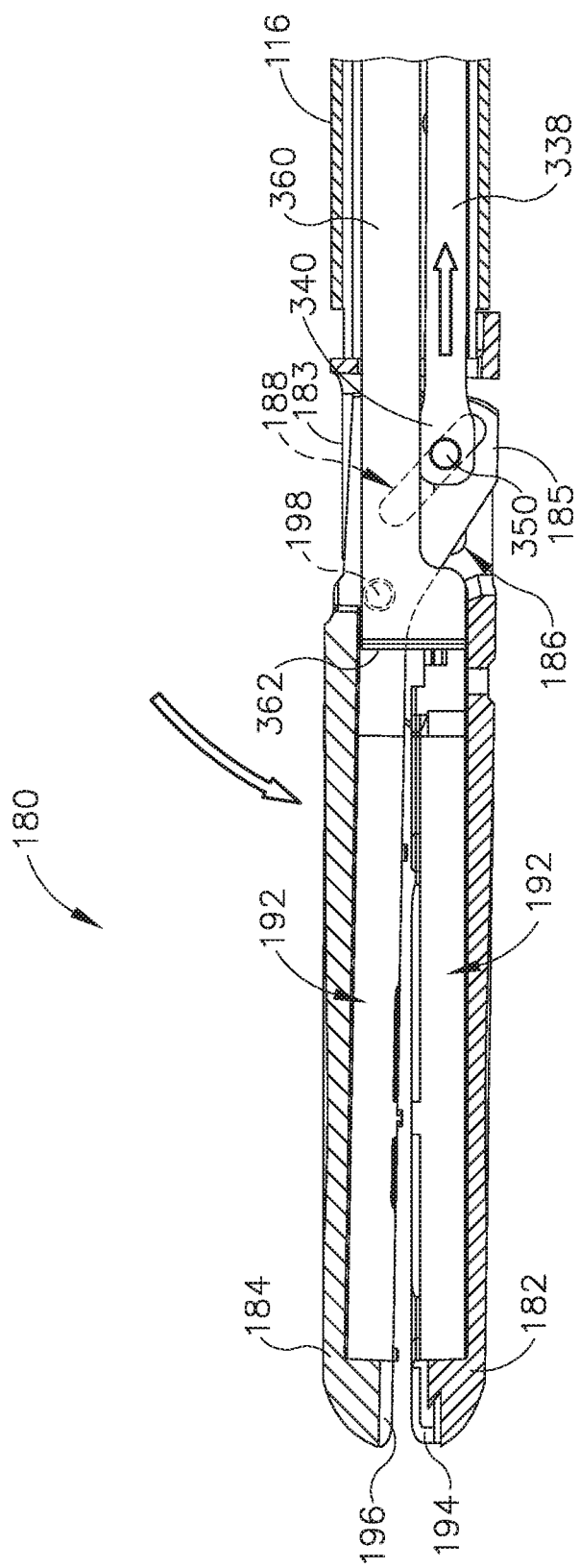
FIG. 8B depicts a cross-sectional side view of the end effector of FIG. 2, where the end effector is in the closed and unfired state, taken along line 8-8 of FIG. 6.
Figure 8C:
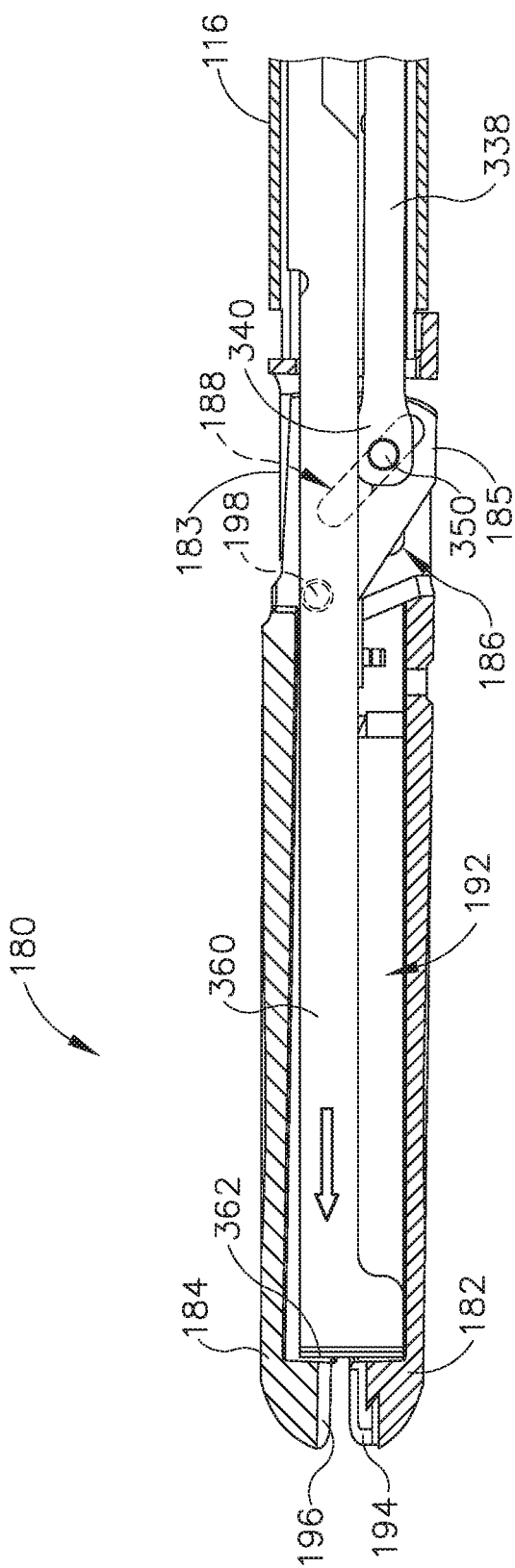
FIG. 8C depicts a cross-sectional side view of the end effector of FIG. 2, where the end effector is in the closed and fired state, taken along line 8-8 of FIG. 6.

Lower jaw (182) and upper jaw (184) also define a knife pathway (192). Knife pathway (192) is configured to slidingly receive knife member (360), such that knife member (360) may be retracted (as shown in FIGS. 8A-8B), and advanced (as shown in FIG. 8C), to cut tissue captured between jaws (182, 184). Lower jaw (182) and upper jaw (184) each comprise a respective electrode surface (194, 196). The power source may provide RF energy to electrode surfaces (194, 196) via electrical wire (15) that extends through handle assembly (120), shaft assembly (140), articulation assembly (110), and electrically couples with one or both of electrode surfaces (194, 196). Electrical wire (15) may selectively activate electrode surfaces (194, 196) in response to an operator pressing activation button (130).

FIGS. 7A-8C show an exemplary use of instrument (100) for end effector (180) to grasp, cut, and seal/weld tissue. As described above, and as shown between FIGS. 7A-7B and 8A-8B, jaw closure trigger (126) may be pivoted toward and away from pistol grip (124) and/or body (122) to open and close jaws (182, 184) of end effector (180) to grasp tissue. In particular, handle assembly (120) further includes a yoke (158) that is slidably coupled along proximal portion (144) of shaft assembly (140). Yoke (158) is coupled with rod portion (332) of jaw closure connector (330) such that translation of yoke (158) relative to proximal portion (144) of shaft assembly (140) translates rod portion (332) of jaw closure connector (330) relative to shaft assembly (140). However, rod portion (332) of jaw closure connector (330) is operable to rotate with proximal portion (144) of shaft assembly (140) relative to yoke (158), such that an operator may rotate knob (134) to rotate end effector (180) about the longitudinal axis defined by shaft assembly (140). In other words, rod portion (332) may rotate with shaft assembly (140), independently of yoke (158); yet rod portion (332) is longitudinally fixed with yoke (158). Any suitable coupling mechanism may be used as would be apparent to one having ordinary skill in the art in view of the teachings herein. For instance, yoke (158) may include an internal recess configured to allow rotation of a coupling member relative to yoke (158), while the internal recess of yoke (158) may abut against side walls of the coupling member to longitudinally drive rod portion (332).

As best seen in FIGS. 7A-7C, yoke (158) is coupled to a body (150) of jaw closure trigger (126) via a link (154). Link (154) is pivotally coupled with yoke (158) via pin (156); while link (154) is also pivotally coupled with body (150) of jaw closure trigger (126) via pin (152). Additionally, jaw closure trigger (126) is pivotally coupled with body (122) of handle assembly (120) via pin (170). Therefore, as shown between FIGS. 7A-7B, an operator may pull jaw closure trigger (126) toward pistol grip (124), thereby rotating jaw closure trigger (126) about pin (170). Rotation of jaw closure trigger (126) leads to rotation of link (154) about both pins (152, 156), which in turn drives yoke (158) in the proximal direction along proximal portion (144) of shaft assembly (140). As described above, jaw closure connector (330) extends within shaft assembly (140), articulation assembly (110), and central channel (190) of lower jaw (182). Additionally, jaw closure connector (330) is also attached to pin (350). Therefore, as seen between FIGS. 8A-8B, proximal translation of yoke (158) leads to proximal translation of pin (350), which in turn cams against slots (188) of proximal arms (185) of upper jaw (184), thereby rotating upper jaw (184) about pivot couplings (198) toward lower jaw (182) such that jaws (182, 184) achieve a closed configuration.

As best seen in FIGS. 7A-7B, yoke (158) is also coupled with a bias spring (155). Bias spring (155) is also coupled to a portion of body (122), such that bias spring (155) biases yoke (158) to the position shown in FIG. 7A (associated with the open configuration of end effector (180) as shown in FIG. 8A). Therefore, if an operator releases jaw closure trigger (126), bias spring (155) will translate yoke (158) to the position shown in FIG. 7A, thereby opening jaws (182, 184) of end effector (180).

As described above, and as shown between FIGS. 7B-7C and 8B-8C, knife trigger (128) may be pivoted toward and away from body (122) and/or pistol grip (124) to actuate knife member (360) within knife pathway (192) of jaws (182, 184) to cut tissue captured between jaws (182, 184). In particular, handle assembly (120) further includes a knife coupling body (174) that is slidably coupled along proximal portion (144) of shaft assembly (140). Knife coupling body (174) is coupled with knife rod (364) of knife member (360) such that translation of knife coupling body (174) relative to proximal portion (144) of shaft assembly (140) translates knife rod (364) and knife member (360) relative to shaft assembly (140). However, knife rod (364) of knife member (360) is operable to rotate with proximal portion (144) of shaft assembly (140) relative to knife coupling body (174), such that an operator may rotate knob (134) to rotate end effector (180) about the longitudinal axis defined by shaft assembly (140). In other words, knife rod (264) may rotate with shaft assembly (140), independently of knife coupling body (174); yet knife rod (264) is longitudinally fixed to knife coupling body (174). Any suitable coupling mechanism may be used as would be apparent to one having ordinary skill in the art in view of the teachings herein. For instance, knife coupling body (174) may include an internal recess that is configured to allow rotation of a coupling member relative to knife coupling body (174), while the internal recess of knife coupling body (174) may abut against side walls of the coupling member to longitudinally drive knife member (360).

As best seen in FIGS. 7B-7C, knife coupling body (174) is coupled to a second pivoting arm (168) via a protrusion (176) of the knife coupling body (174) and a slot (172) defined by second pivoting arm (168). Second pivoting arm (168) is pivotally coupled with body (122) of handle assembly (120) via pin (170). Second pivoting arm (168) is coupled to a first pivoting arm (160) via a protrusion (166) of second pivoting arm (168) and a slot (164) defined by first pivoting arm (160). First pivoting arm (160) is pivotally connected to a pin (162) and is unitarily attached to knife trigger (128). Therefore, as knife trigger (128) pivots toward body (122) and/or pistol grip (124), first pivoting arm (160) pivots about pin (162) in a first angular direction. As first pivoting arm (160) pivots about pin (162), second pivoting arm (168) pivots about pin (170) in a second, opposite, angular direction due to slot (164) actuating protrusion (166). As second pivoting arm (168) pivots about pin (170) in the second angular direction, knife coupling body (174) translates along proximal portion (144) of shaft assembly (140) due to slot (172) actuating protrusion (176) of knife coupling body (174). Because knife coupling body (174) is coupled to knife member (360), knife member (360) translates distally within shaft assembly (140), articulation assembly (110), and within knife pathway (192) of end effector (180), as best shown between FIGS. 8B-8C. Knife member (360) includes distal cutting edge (362) that is configured to sever tissue captured between jaws (182, 184). Therefore, pivoting knife trigger (128) causes knife member (360) to actuate within knife pathway (192) of end effector (180) to sever tissue captured between jaws (182, 184).

As best seen in FIGS. 7B-7C, knife trigger (128) is biased to the positions shown in FIG. 7A-7B by a bias arm (129). Bias arm (129) may include any suitable biasing mechanism as would be apparent to one having ordinary skill in the art in view of the teachings herein. For instance, bias arm (129) may include a torsion spring. Bias arm (129) is also coupled to a portion of body (122), such that bias arm (129) biases knife trigger (128) to the position shown in FIG. 7A-7B (associated with the knife member (360) in the retracted position). Therefore, if an operator releases knife trigger (128), bias arm (129) returns knife trigger (128) to the position shown in FIGS. 7A-7B, thereby translating knife member (360) toward the retracted position.

With distal cutting edge (362) of knife actuated to the advance position (position shown in FIG. 8C), an operator may press activation button (130) to selectively activate electrode surfaces (194, 196) of jaws (182, 184) to weld/seal severed tissue that is captured between jaws (182, 184).

As described above, and as best shown between FIGS. 9A-10C, rotation of articulation control (132) relative to body (122) of hand assembly (120) will drive deflection of end effector (180) from the longitudinal axis defined by shaft assembly (140) from a non-articulated configuration (FIG. 10A) to an articulated configuration (FIGS. 10B-10C). In particular, as best shown in FIGS. 9A-9C, handle assembly (120) further includes an articulation drive assembly (200). Articulation drive assembly (200) includes a rotatable housing (220) that is unitarily connected to articulation control (132), such that rotation of articulation control (132) relative to body (122) leads to rotation of rotatable housing (220) relative to body (122). Half of rotatable housing (220) is purposely omitted from FIGS. 9A-9C for purposes of clarity.

Rotatable housing (220) and articulation control (132) are rotatably coupled to a distal cap (202) and a proximal cap (210), which are both fixed to body (122) of handle assembly (120). Rotatable housing (220) includes a first internal threading (222) and a second internal threading (224). First internal threading (222) is threaded in an opposite orientation/direction as compared to second internal threading (224).

Additionally, articulation drive assembly (200) includes a first lead screw assembly (230) and a second lead screw assembly (250) slidably coupled along proximal portion (144) of shaft assembly (140). First lead screw assembly (230) and second lead screw assembly (250) each have pins (204) extending through them. Pins (204) are fixed to proximal cap (210) and distal cap (202). Therefore, pins (204) are rotationally fixed relative to body (122) of handle assembly (120). Because pins (204) extend through lead screw assemblies (230, 250), lead screw assemblies (230, 250) are also rotationally fixed relative to body (122) of handle assembly (120). However, first lead screw assembly (230) and second lead screw assembly (250) are slidably attached to pins (204). Therefore, lead screw assemblies (230, 250) may translate, without rotating, along pins (204) and proximal portion (144) of shaft assembly (140) within the confines of rotatable housing (220).

First lead screw assembly (230) includes threading (232) that is configured to mesh with first internal threading (222) of rotatable housing (220). Second lead screw assembly (250) includes threading (252) that is configured to mesh with second internal threading (224) of rotatable housing (220). Because lead screw assemblies (230, 250) are rotationally fixed relative to body (122), and because each lead screw assembly (230, 250) has threading (232, 252) that meshes with internal threading (222, 224) having opposing orientation/direction, rotation of rotatable housing (220) in one direction leads to simultaneous translation of lead screw assemblies (230, 250) in opposing longitudinal directions. In other words, rotation of rotatable housing (220) causes first and second internal threading (222, 224) to cam against threading (232, 252) of lead screw assemblies (230, 250) respectively, such that longitudinal actuating lead screw assemblies (230, 250) in opposite longitudinal directions. For instance, if an operator rotates articulation control (132) and rotatable housing (220) in a first rotational direction, lead screw assemblies (230, 250) will translate away from each other (as shown between FIGS. 9A-9B) due to rotation of internal threading (222, 224) causing contact with threading (232, 252) of lead screw assemblies (230, 250), respectively. However, if an operator rotates articulation control (132) and rotatable housing (220) in a second rotational direction, lead screw assemblies (230, 250) will translate toward each other (as shown between FIGS. 9A and 9C) due to rotation of internal threading (222, 224) causing contact with threading (232, 252) of lead screw assemblies (230, 250), respectively.

As will be described in greater detail below, each lead screw assembly (230, 250) is coupled with a respective rod portion (302) of articulation connectors (300) such that translation of lead screw assemblies (230, 250) relative to proximal portion (144) of shaft assembly (140) translates rod portions (302) of articulation connectors (300) relative to shaft assembly (140). However, rod portions (302) of articulation connectors (300) are operable to rotate with proximal portion (144) of shaft assembly (140) relative to their respective lead screw assemblies (230, 250), such that an operator may rotate knob (134) to rotate end effector (180) about the longitudinal axis defined by shaft assembly (140). In other words, articulation connectors (300) may rotate with shaft assembly (140) independently of lead screw assemblies (230, 250), yet articulation connectors (300) are longitudinally fixed with lead screw assemblies (230, 250). Any suitable coupling mechanism may be used as would be apparent to one having ordinary skill in the art in view of the teachings herein. For instance, lead screw assemblies (230, 250) may each include an internal recess configured to allow rotation of a coupling member relative to lead screw assemblies (230, 250), while the internal recess of lead screw assemblies (230, 250) may abut against side walls of the coupling member to longitudinally drive articulation connection (300).

As mentioned above, articulation connector (300) includes rod portions (302) that are configured to longitudinally translate relative to shaft assembly (140) by coupling with lead screw assemblies (230, 250). As also described above, each articulation connector (300) include a flexible band portion (308) slidably disposed within articulation assembly (110) of instrument (100); while articulation connectors (300) each include a distal coupling portion (310) fixed to proximal body (183) of lower jaw (182). Distal coupling portion (310) may be fixed to proximal body (183) of lower jaw (182) through any suitable means known to a person having ordinary skill in the art in view of the teachings herein, such as welding. As also mentioned above, articulation assembly (110) also includes flexible members (116) that are configured to bend relative to the longitudinal axis defined by the shaft assembly (140) to allow end effector (180) to deflect relative to the longitudinal axis defined by shaft assembly (140).

In an exemplary use, an operator may rotate articulation control (132) and rotatable housing (220) in a first rotational direction such that lead screw assemblies (230, 250) translate away from each other (as shown between FIGS. 9A-9B), as described above. Because lead screw assemblies (230, 250) are each coupled to a respective articulation connector (300), each articulation connector (300) translates with its respective lead screw assembly (230, 250). Therefore, articulation connectors (300) translate in opposing directions in response to rotation of articulation control (131) and rotatable housing (220). As described above, articulation connectors (300) are attached to proximal body (183) of lower jaw (182) via distal coupling portions (310). In particular, distal coupling portion (310) of each articulation connector (300) is attached to an opposite side of proximal body (183) of lower jaw (182). As best shown in FIG. 10B, opposing translation of articulation connectors (300) causes one articulation connector (300) to drive end effector (180) proximally, while causing another articulation connector (300) chive end effector (180) distally, thereby articulating end effector (180) and flexible member (116) of articulation assembly (110) to a first articulated configuration. Band portion (348) and portions of knife member (360) within central pathway (113) are also flexible to bend with flexible member (116). The degree to which end effector (180) articulates relative to the longitudinal axis defined by shaft assembly (140) may be determined by the longitudinal distance lead screw assemblies (230, 250) travel away from each other compared to their positions shown in FIG. 9A. Therefore, an operator may choose the degree at which end effector (180) articulates based on the rotational displacement of articulation control (132) from its home position shown in HG. 9A.

Additionally, an operator may rotate articulation control (132) and rotatable housing (220) in a second rotational direction such that lead screw assemblies (230, 250) translate toward each other (as shown between FIGS. 9A and 9C). Because lead screw assemblies (230, 250) are each coupled to a respective articulation connector (300), each articulation connector (300) translates with its respective lead screw assembly (230, 250). Therefore, articulation connectors (300) translate in opposing directions. As best shown in FIG. 10C, translation of articulation connectors (300) leads to end effector (180) being driven to a second articulated configuration. As described above, articulation connectors (300) are attached to a proximal body (183) of lower jaw (182) via distal coupling portions (310). In particular, distal coupling portion (310) of each articulation connector (300) is attached to an opposite side of proximal body (183) of lower jaw (182). As best shown in FIG. 10C, opposing translation of articulation connectors (300) causes one articulation connector (300) to drive end effector (180) proximally, while causing another articulation connector (300) to drive end effector (180) distally, thereby articulating end effector (180) and flexible member (116) of articulation assembly (110) to a second articulated configuration.

In addition to or in lieu of the foregoing, instrument (100) may be further constructed and operable in accordance with at least some of the teachings of U.S. patent application Ser. No. 15/214,415, entitled "Articulation Joint Having an Inner Guide," filed Jul. 19, 2016, issued as U.S. Pub. No. 2018/0021051 on Jan. 25, 2018, the disclosure of which is incorporated by reference herein.

II. Exemplary Alternative Articulation Assembly with Wedging Adapter

In some instances, it may be desirable to provide electrical insulation between external sheath (146) and articulation assembly (110). It may also be desirable to provide enhanced stiffness in the articulation assembly (110) when articulation assembly (110) is under a tensile load, particularly when jaw closure connector (330) is retracted proximally to drive upper jaw (184) toward lower jaw (182), to prevent such a tensile load from compromising a straight or articulated configuration of articulation assembly (110). FIGS. 11-17 show an exemplary alternative articulation assembly (400) that may be readily incorporated into instrument (100) in place of articulation assembly (110). Articulation assembly (400) is longitudinally interposed between a shaft assembly (420) and an end effector (410). Shaft assembly (420) of this example comprises an electrically conductive (e.g., metallic) external sheath (422) and is otherwise configured and operable like shaft assembly (140). In some other variations, external sheath (422) is formed of a non-conductive (e.g., non-metallic) material. End effector (410) of this example comprises an upper jaw (412) and a lower jaw (414) and is otherwise configured and operable like end effector (180).

Figure 12:
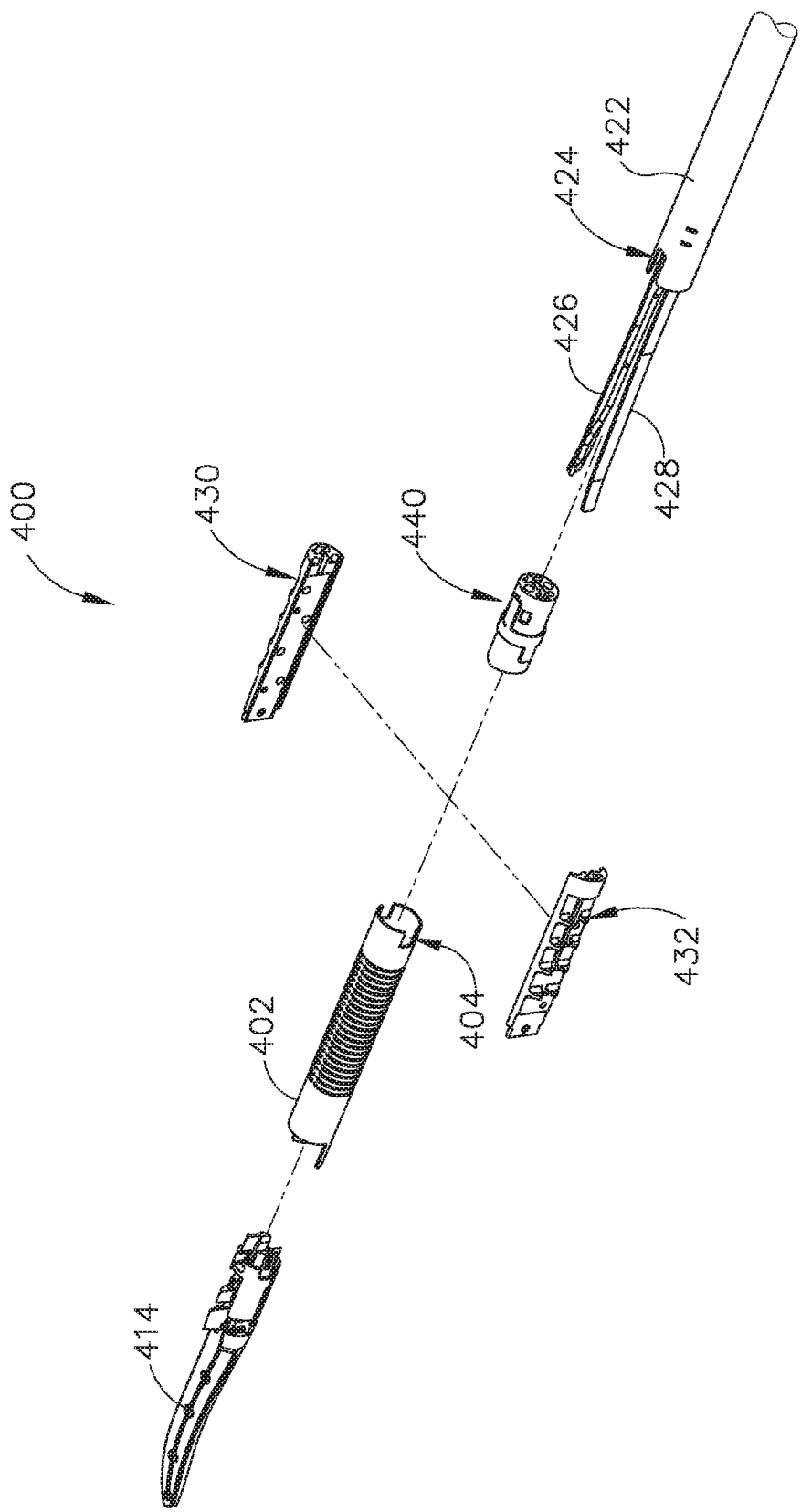
FIG. 12 depicts an exploded perspective view of the articulation assembly of FIG. 11.
Figure 13:
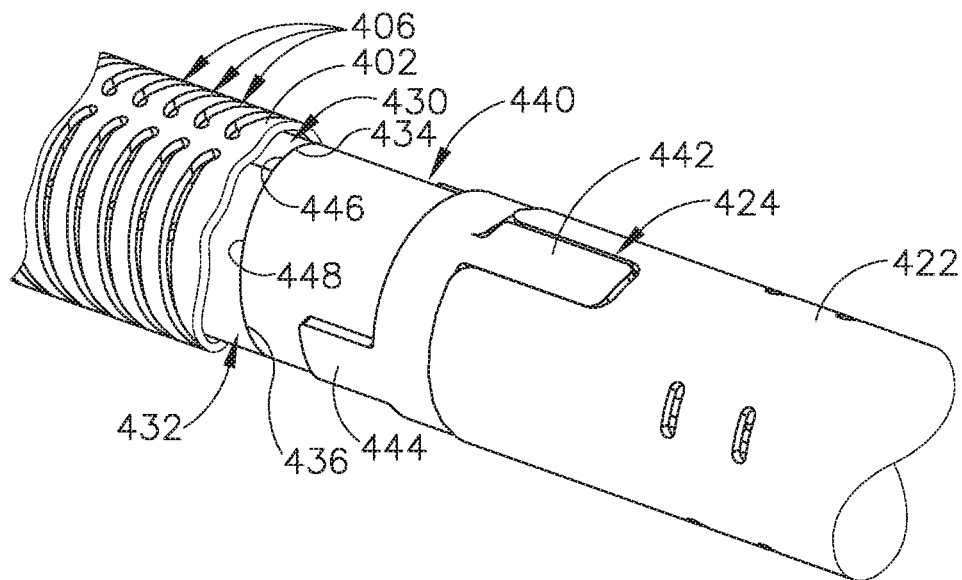
FIG. 13 depicts a perspective view of a proximal portion of the articulation assembly of FIG. 11, with a portion of an outer sleeve omitted to reveal internal structures.

Except as otherwise described below, articulation assembly (400) may be configured and operable like articulation assembly (110). As best seen in FIG. 12, articulation assembly (400) of the present example comprises an outer sleeve (402), a pair of frame members (430, 432), and an adapter member (440). Outer sleeve (402) of the present example comprises a single piece of conductive material (e.g., metal) with a plurality of angularly extending slits (406) formed therein. In some other variations, outer sleeve (402) is formed of a non-conductive (e.g., non-metallic) material. As best seen in FIG. 13, slits (406) are spaced apart from each other along a portion of the length of outer sleeve (402). Slits (406) allow outer sleeve (402) to flex along only one plane. In the present example, that plane of flexure is perpendicular to the plane along which upper jaw (412) pivots relative to lower jaw (414). The distal end of outer sleeve (402) is fixedly secured relative to lower jaw (414).

Figure 14:
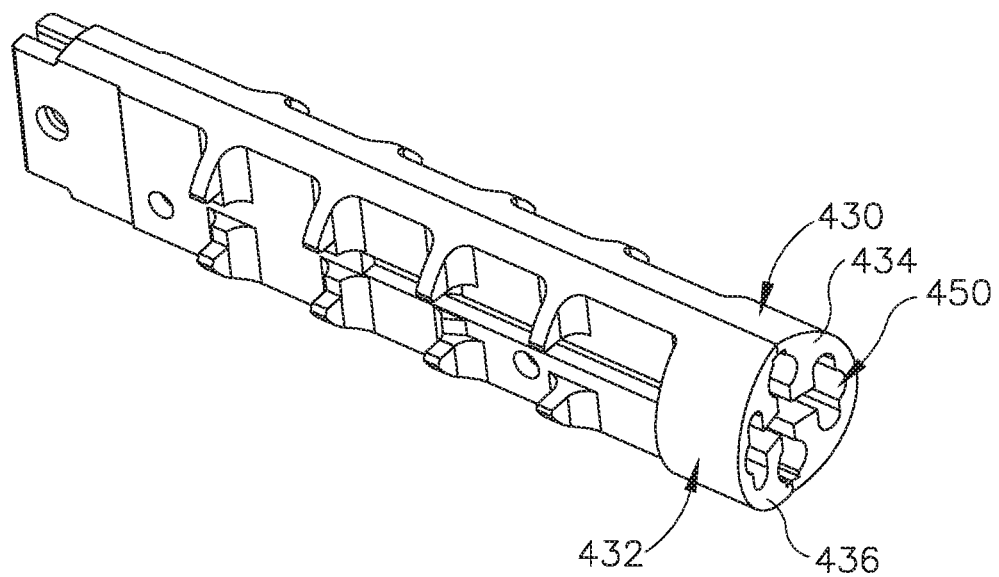
FIG. 14 depicts a perspective view of frame members of the articulation assembly of FIG. 11.
Figure 15:
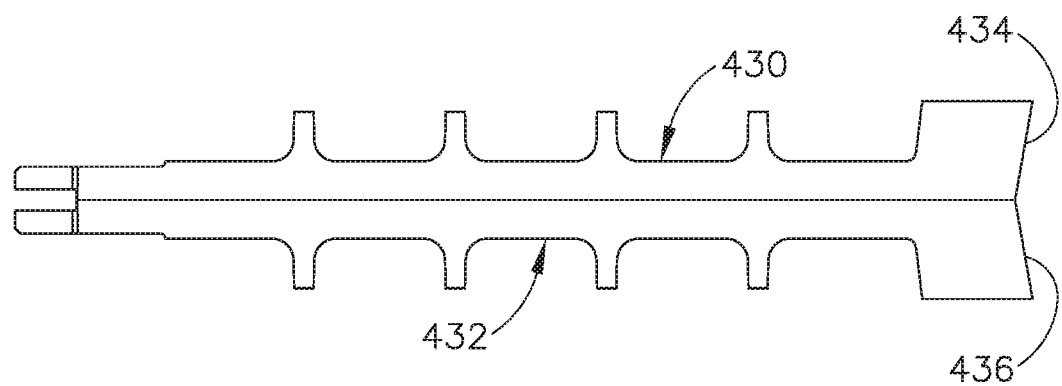
FIG. 15 depicts a top plan view of the frame members of FIG. 14.

As best seen in FIG. 14, frame members (430, 432) are configured to be joined together laterally. Frame members (430, 432) include channels (450) that are configured to slidably receive band portions (426, 428), which are shown in FIG. 12, and which are configured and operable like band portions (308) to drive articulation of articulation assembly (400). Frame members (430, 432) also include channels (450) that are configured to slidably receive a knife rod (not shown) like knife rod (364), a rod portion (not shown) like rod portion (332), and an electrical wire (not shown) like electrical wire (15). Frame members (430, 432) are configured to flex laterally along only one plane. In the present example, that plane of flexure is perpendicular to the plane along which upper jaw (412) pivots relative to lower jaw (414). Frame members (430, 432) are disposed within outer sleeve (402), such that frame members (430, 432) flex laterally with outer sleeve (402). As best seen in FIG. 15, the proximal ends of frame members (430, 432) include proximally facing cam surfaces (434, 436), which will be described in greater detail below. The distal ends of frame members (430, 432) are fixedly secured relative to lower jaw (414).

Figure 16:
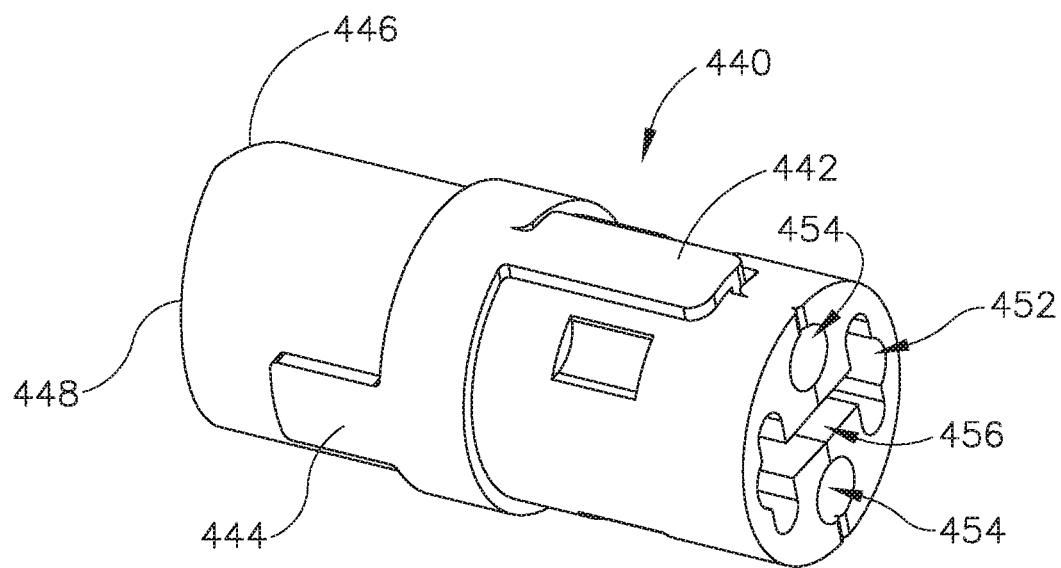
FIG. 16 depicts a perspective view of an adapter member of the articulation assembly of FIG. 11.
Figure 17:
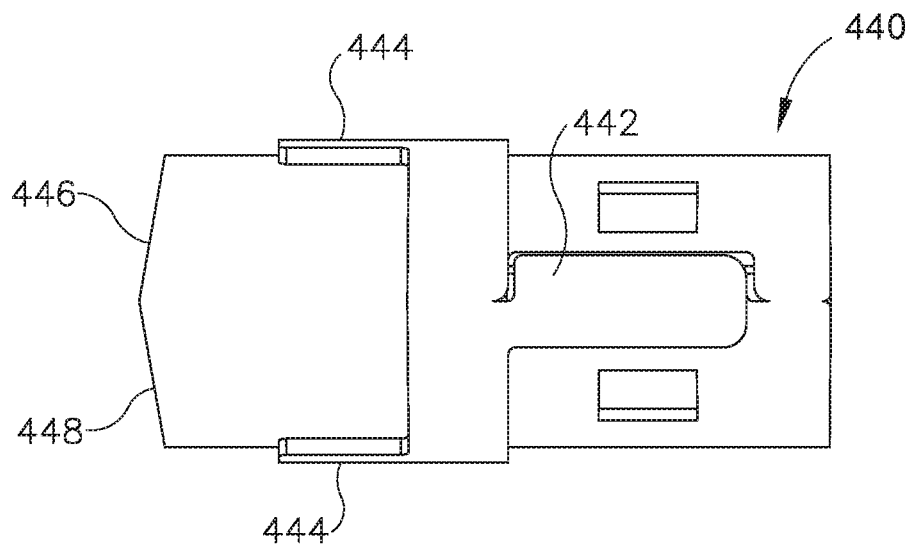
FIG. 17 depicts a top plan view of the adapter member of FIG. 16.

As best seen in FIGS. 16-17, adapter member (440) includes a proximally extending alignment member (442), a pair of distally extending alignment members (444), pair of distally facing cam surfaces (446, 448), a pair of band channels (452), and a pair of rod channels (454). Proximally extending alignment member (442) is configured to fit in a distally presented notch (424) at the distal end of external sheath (422), thereby providing alignment between adapter member (440) and external sheath (422) and preventing adapter member (440) from rotating relative to external sheath (422). In some variations, adapter member (440) includes a pair of alignment members (442) to complement a pair of distally presented notch (424) at the distal end of external sheath (422). Distally extending alignment members (444) are configured to fit in proximally presented notches (404) at the proximal end of outer sleeve (402), thereby providing alignment between adapter member (440) and outer sleeve (402) and preventing adapter member (440) from rotating relative to outer sleeve (402).

Band channels (452) are configured to align with corresponding channels (450) of frame members (430, 432) and slidably receive band portions (426, 428). Rod channels (454) are configured to align with corresponding channels (450) of frame members (430, 432) and slidably receive the knife rod (not shown) like knife rod (364) and the rod portion (not shown) like rod portion (332). A channel (456) extending between band channels (452) is configured to align with a corresponding channel (450) of frame members (430, 432) and receive electrical wire (not shown) like electrical wire (15). Adapter member (440) of the present example is formed of a material that is electrically non-conductive (e.g., plastic). Adapter member (440) thus provides electrical insulation between outer sleeve (402) and external sheath (422). Adapter member (440) further provides electrical insulation between external sheath (42 and the components that are disposed in channels (452, 454, 456).

Cam surfaces (446, 448) of adapter member (440) are configured to complement cam surfaces (434, 436) of frame members (430, 432). As best seen in FIG. 13, cam surface (446) engages cam surface (434); and cam surface (448) engages cam surface (436). Due to the configurations and relationships of cam surfaces (434, 436, 446, 448), adapter member (440) acts as a wedge and thereby drives frame members (430, 432) laterally away from each other when articulation assembly (400) is placed under a proximally oriented, tensile load. When frame members (430, 432) are driven apart from each other, frame members (430, 432) are driven into the inner surface of outer sleeve (402). Frame members (430, 432) thus encounter lateral compression between cam surfaces (446, 448) of adapter member (440) and the inner surface of outer sleeve (402) when articulation assembly (400) is placed under a proximally oriented, tensile load. In the present example, band portions (426, 428) are already pre-loaded with a certain tensile load, such that frame members (430, 432) always encounter some degree of lateral compression between cam surfaces (446, 448) of adapter member (440) and the inner surface of outer sleeve (402). The proximally oriented, tensile load may be further enhanced when jaw closure connector (330) is retracted proximally to drive upper jaw (184) toward lower jaw (182).

When frame members (430, 432) are laterally compressed between cam surfaces (446, 448) of adapter member (440) and the inner surface of outer sleeve (402), such compression may provide enhanced rigidity to articulation section (400) which may in turn secure the straight or articulated configuration of articulation section (400). Thus, closure of jaws (182, 184) should not compromise the straight or articulated configuration of articulation section (400).

III. Exemplary Alternative Outer Sleeves for Articulation Assembly

As indicated above, it may be desirable to provide an articulation assembly with an outer sleeve (402) that is capable of flexing laterally along only one plane (i.e., along a plane that is perpendicular to the plane along which upper jaw (412) pivots relative to lower jaw (414)), with a substantial articulation angle (e.g., up to at least 50° articulation angle). It may thus be desirable for the articulation assembly and outer sleeve (402) to be substantially rigid along the plane through which upper jaw (412) pivots relative to lower jaw (414). FIGS. 18-23 show exemplary alternative outer sleeves (500, 550) that may be used in place of outer sleeve (402). Each outer sleeve (500, 550) may provide lateral flexure along only one plane; while also providing substantial rigidity along the plane through which upper jaw (412) pivots relative to lower jaw (414).

Figure 18:
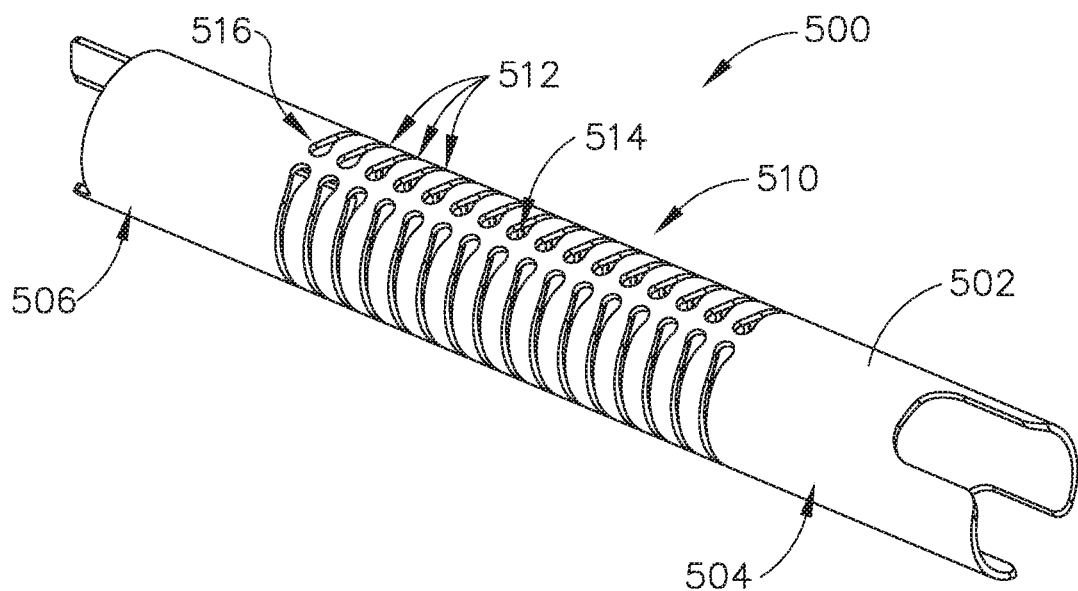
FIG. 18 depicts a perspective view of an exemplary alternative outer sleeve that may be incorporated into an articulation assembly.
Figure 19:
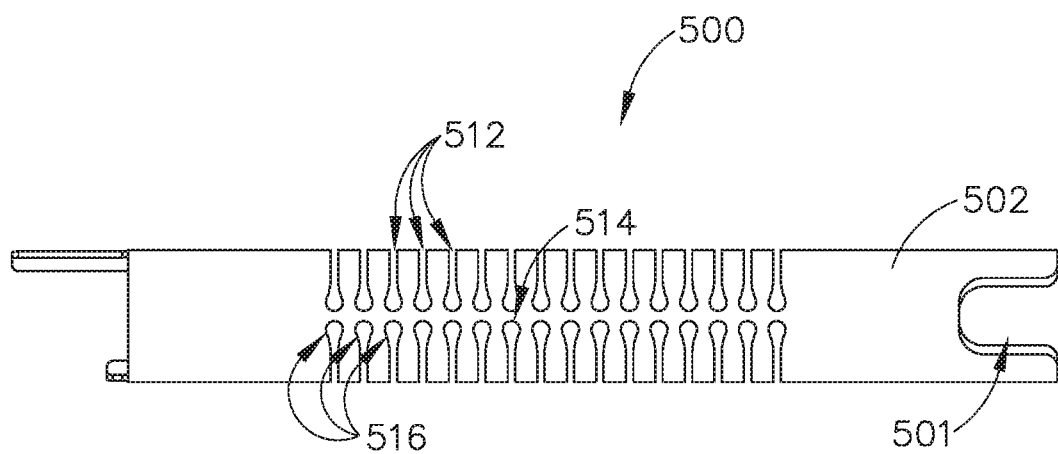
FIG. 19 depicts a top plan view of the outer sleeve of FIG. 18.
Figure 23:
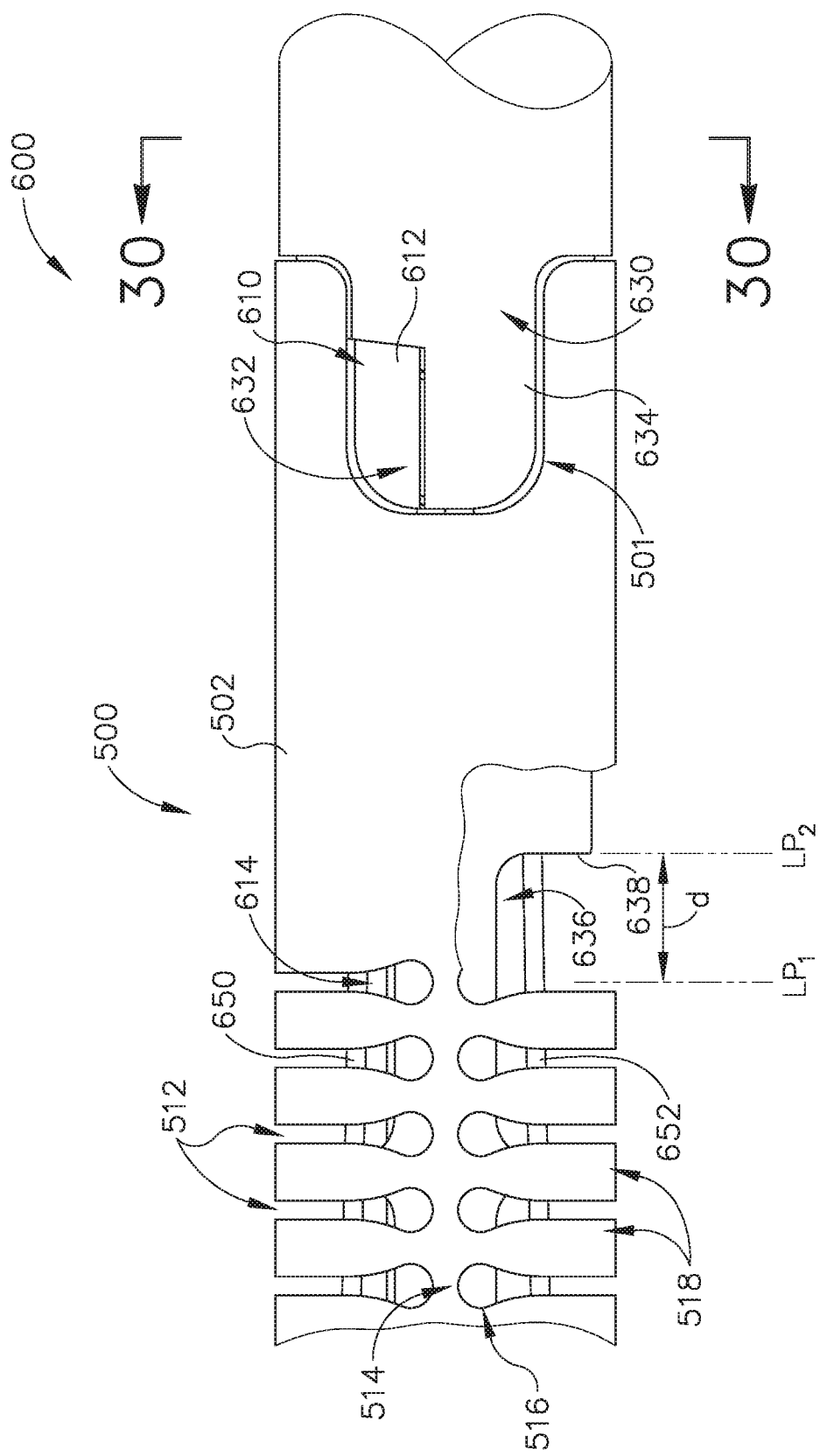
FIG. 23 depicts a partial top plan view of an exemplary alternative articulation assembly incorporating the outer sleeve of FIG. 19, with a portion of the outer sleeve omitted to reveal internal structures.

As shown in FIGS. 18-19 and 23, outer sleeve (500) includes a body (502) having a rigid proximal portion (504), a rigid distal portion (506), and a flexible portion (510) that is longitudinally interposed between rigid portions (504, 506). Flexible portion (510) includes an array of slits (512), which are spaced apart from each other along the length of flexible portion (510). Each slit (512) extends along an angular extent that is less than 180°. Each slit (512) angularly terminates in a pair of lobes or widened portions (516). Widened portions (516) are teardrop-shaped in the present example. Spines (514) extend continuously between rigid proximal and distal portions (504, 506), in the angular regions between corresponding widened portions (516) of slits (512). Spines (514) each extend along the transverse plane along which outer sleeve (500) is rigid. Spines (514) and slits (512) cooperate to form a set of ribs (518), which are longitudinally interposed between slits (512). Ribs (518) extend about the circumference of outer sleeve (500), angularly terminating at spines (514).

In the present example, the inclusion of widened portions (516) enables ribs (518) to have a relatively large thickness, providing greater separation between slits (512), without adversely impacting the lateral flexibility of outer sleeve (500). With greater separation between slits (512), fewer slits (512) are needed, thereby making it easier to manufacture outer sleeve (500). Also in the present example, slits (512) are wider than slits (406). Ultimately, the above-noted structural features of outer sleeve (500) may provide a substantial articulation angle (e.g., up to at least 50°), minimize strain in outer sleeve (500), improve manufacturability of outer sleeve (500), and/or reduce the cost of outer sleeve (500).

Figure 20:
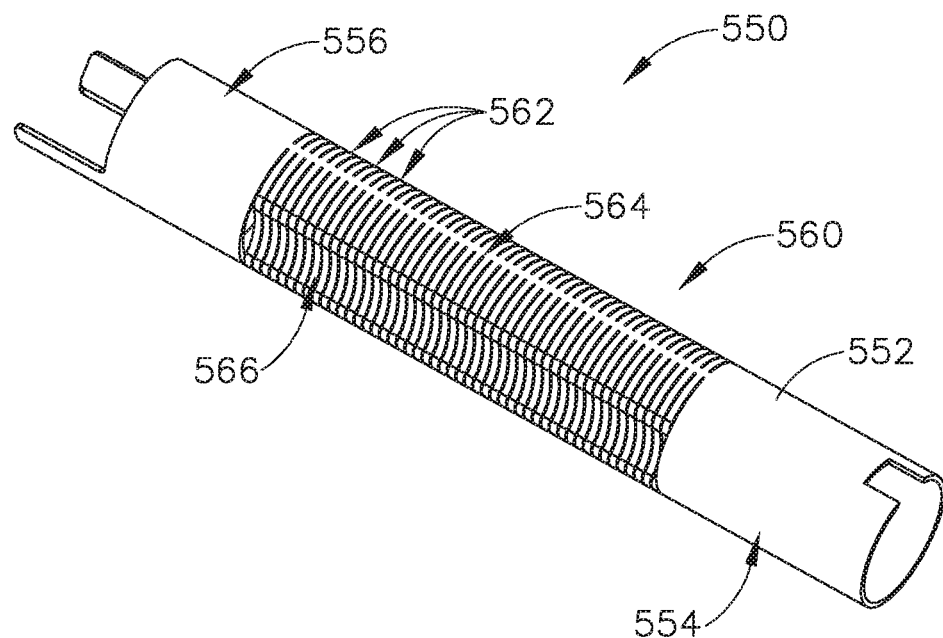
FIG. 20 depicts a perspective view of another exemplary alternative outer sleeve that may be incorporated into an articulation assembly.
Figure 21:
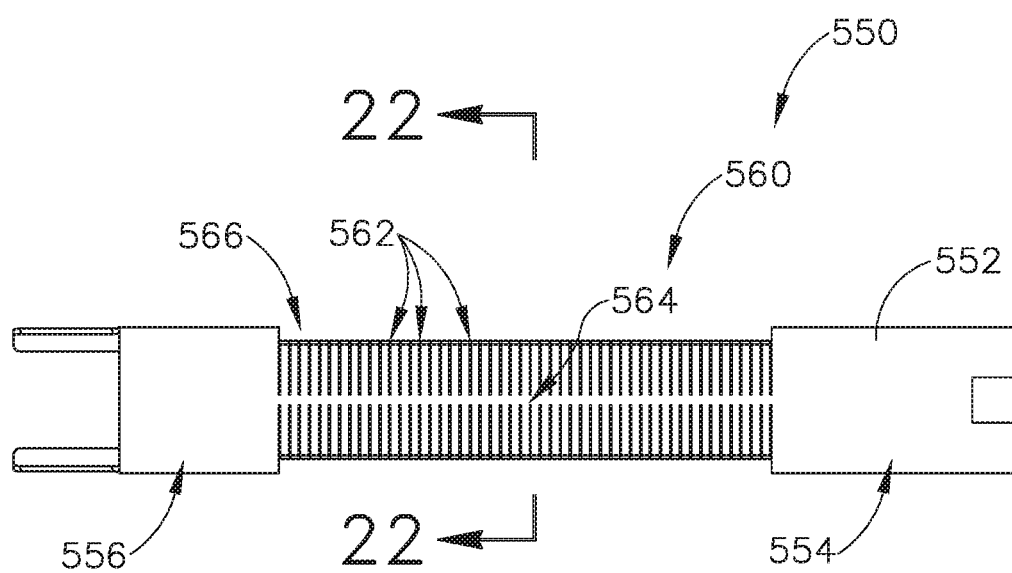
FIG. 21 depicts a top plan view of the outer sleeve of FIG. 20.
Figure 22:
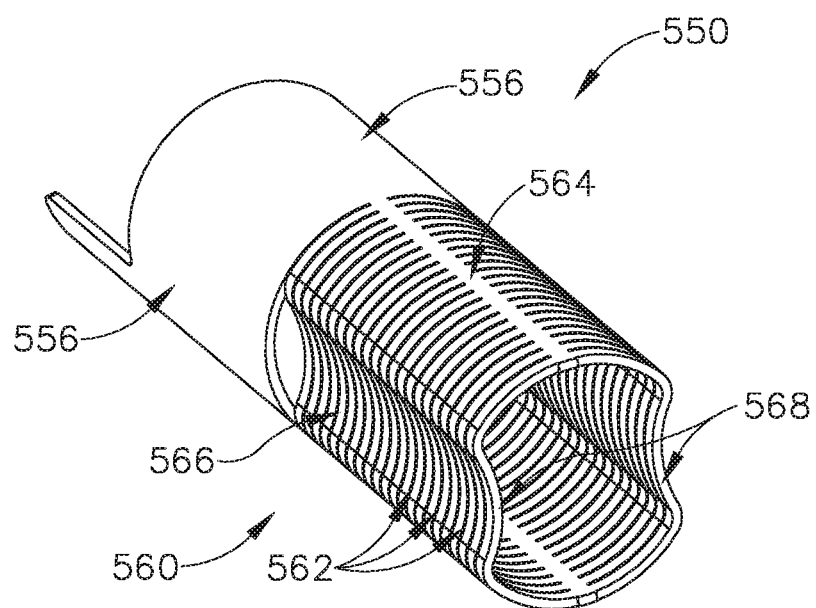
FIG. 22 depicts a perspective cross-sectional view of the outer sleeve of FIG. 22, taken along line 22-22 of FIG. 21.

As shown in FIGS. 20-22, outer sleeve (550) includes a body (552) having a rigid proximal portion (554), a rigid distal portion (556), and a flexible portion (560) that is longitudinally interposed between rigid portions (554, 556). Flexible portion (560) includes an array of slits (562), which are spaced apart from each other along the length of flexible portion (560). Each slit (562) extends along an angular extent that is less than 180°. Spines (564) extend continuously between rigid proximal and distal portions (554, 556), in the angular regions between slits (562). Spines (564) each extend along the transverse plane along which outer sleeve (550) is rigid. Spines (564) and slits (562) cooperate to form a set of ribs (568), which are longitudinally interposed between slits (562). Ribs (568) extend about the longitudinal axis of outer sleeve (550), angularly terminating at spines (564).

Ribs (568) also include concave bends (566) in the present example. Concave bends (566) extend along the entire length of flexible portion (560). As best seen in FIG. 22 concave bends (566) are configured and positioned such that the lateral width of flexible portion (560) is minimized along a plane that is perpendicular to a plane along which spines (564) extend. In particular, concave bends (566) are configured and positioned such that the lateral width of flexible portion (560) is minimized along the plane along which flexible portion (560) flexes. In the present example, the presence of concave bends (566) allows flexible portion (560) to amplify the effects of articulation. By "amplifying" the effects of articulation, flexible portion (560) provides a greater degree of lateral deflection in response to opposing longitudinal translation of band portions (308, 426, 428). For instance, providing a reduced width along flexible portion (560) may require band portions (308, 426, 428) to be positioned laterally closer to each other; and this enhanced lateral proximity between band portions (308, 426, 428) may provide a corresponding enhanced degree of lateral deflection of flexible portion (560) as band portions (308, 426, 428) are longitudinally translated in opposite directions simultaneously.

In some instances, an enhanced degree of lateral deflection may present an enhanced risk of band portions (308, 426, 428) laterally buckling during articulation. However, the presence of concave bends (566) may further provide enhanced lateral stability along and within outer sleeve (550). In particular, concave bends (566) may prevent band portions (308, 426, 428) from inadvertently buckling and thereby deflecting laterally out through flexible portion (560) when outer sleeve (550) is in a laterally bent state.

Figure 24:
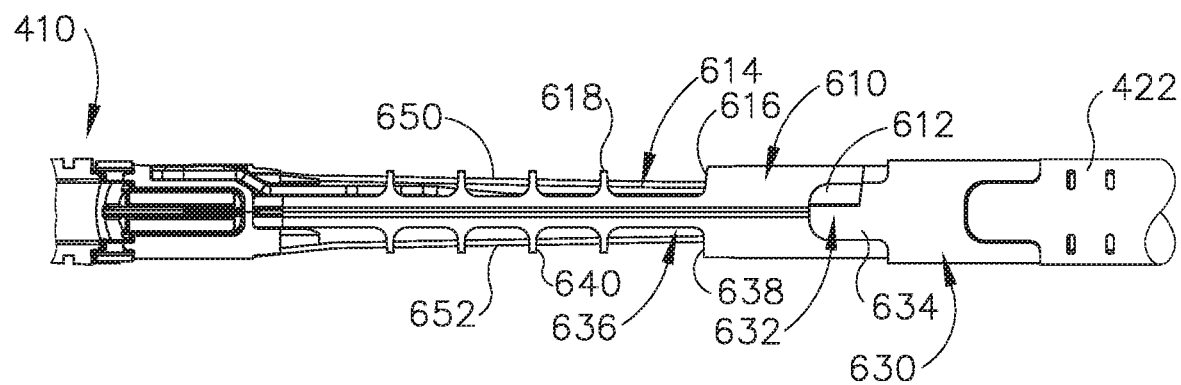
FIG. 24 depicts a top plan view of the articulation assembly of FIG. 23, with the outer sleeve omitted.
Figure 25:
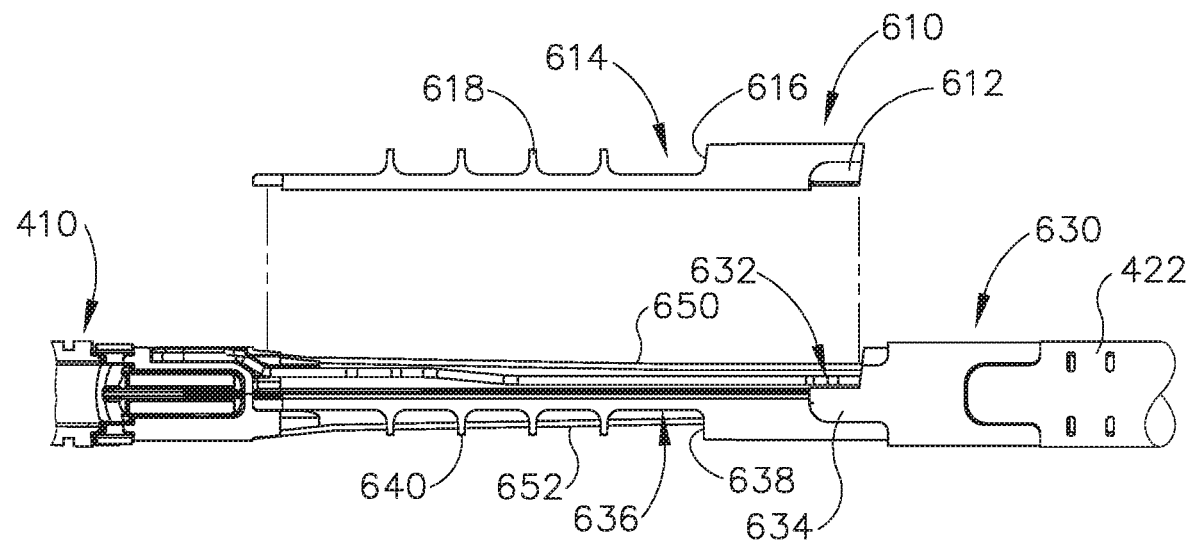
FIG. 25 depicts a partially exploded top plan view of the articulation assembly of FIG. 23, with the outer sleeve omitted.
Figure 26:
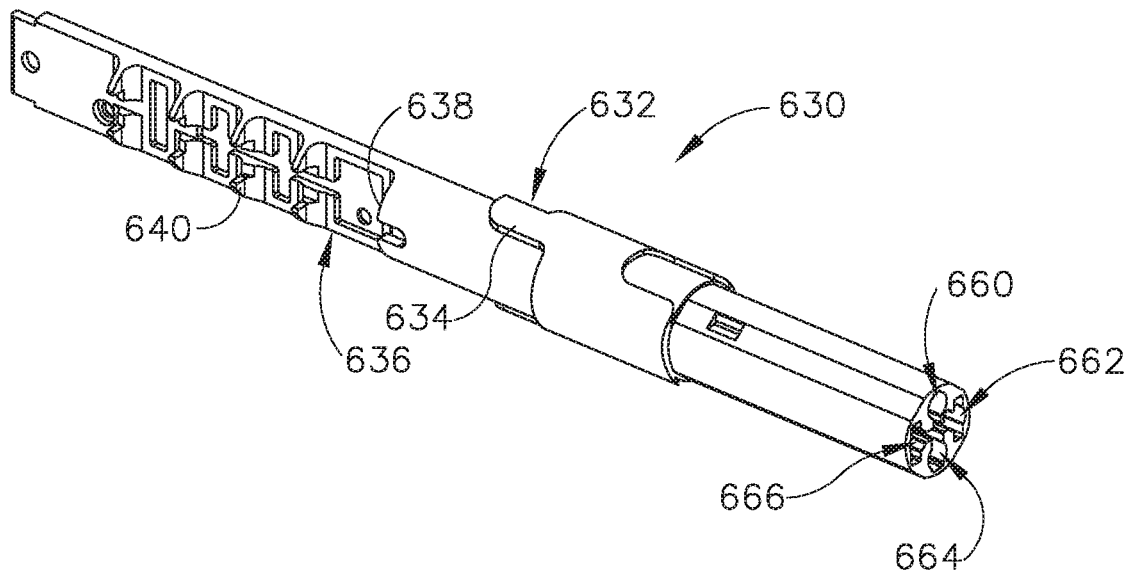
FIG. 26 depicts a perspective view of a frame member of the articulation assembly of FIG. 23.

IV. Exemplary Alternative Articulation Assembly with Staggered Frame Members FIGS. 23-30 show another exemplary alternative articulation assembly (600) that may be used in place of articulation assembly (110, 400). Articulation assembly (600) of this example includes outer sleeve (500), though any other suitable outer sleeve (402, 550) may instead be used. Articulation assembly (600) further includes a first frame member (610) and a second frame member (630). As best seen in FIGS. 24-25, frame members (610, 630) are configured to laterally join with each other. However, frame members (610, 630) are not symmetric with each other. Instead, a proximal portion of frame member (630) extends proximally relative to the proximal end of frame member (610), such that frame members (610, 630) are in a longitudinally staggered configuration. This proximal portion of frame member (630) is configured to operate similar to adapter member (440) described above. Also in the present example, with the proximal portion of frame member (630) being longitudinally interposed between outer sleeve (500) and external sheath (422), frame member (630) is formed of an electrically non-conductive material (e.g., plastic), such that frame member (630) provides electrical insulation between outer sleeve (500) and external sheath (422). Frame member (630) further provides electrical insulation between externals sheath (422) and the components that extend longitudinally through frame member (630) as described in greater detail below.

As best seen in FIGS. 24-25, first frame member (610) includes a proximal alignment feature portion (612), a narrowed region (614), a distally presented surface (616) providing a transition to narrowed region (614), and a set of laterally extending ribs (618). Second frame member (630) includes a proximal lateral recess (632), a proximal alignment feature portion (634), a narrowed region (636), a distally presented surface (638) providing a transition to narrowed region (636), and a set of laterally extending ribs (618). The proximal end of first frame member (610) is configured to fit in proximal lateral recess (632) of second frame member (630). In some versions, frame members (610, 630) are ultrasonically welded at this region where the proximal end of first frame member (610) is received in proximal lateral recess (632). In some other versions, these regions are joined together by an adhesive, snap fitting, a clasp, by overlapping structural features, and/or using any other suitable structural configurations and/or techniques. Various suitable ways in which frame members (610, 630) may be secured together will be apparent to those of ordinary skill in the art in view of the teachings herein. Also in the present example, the distal ends of frame members (610, 630) terminate the same longitudinal position (i.e., at the same plane extending transversely relative to the longitudinal axis of shaft assembly (420)).

Figure 30:
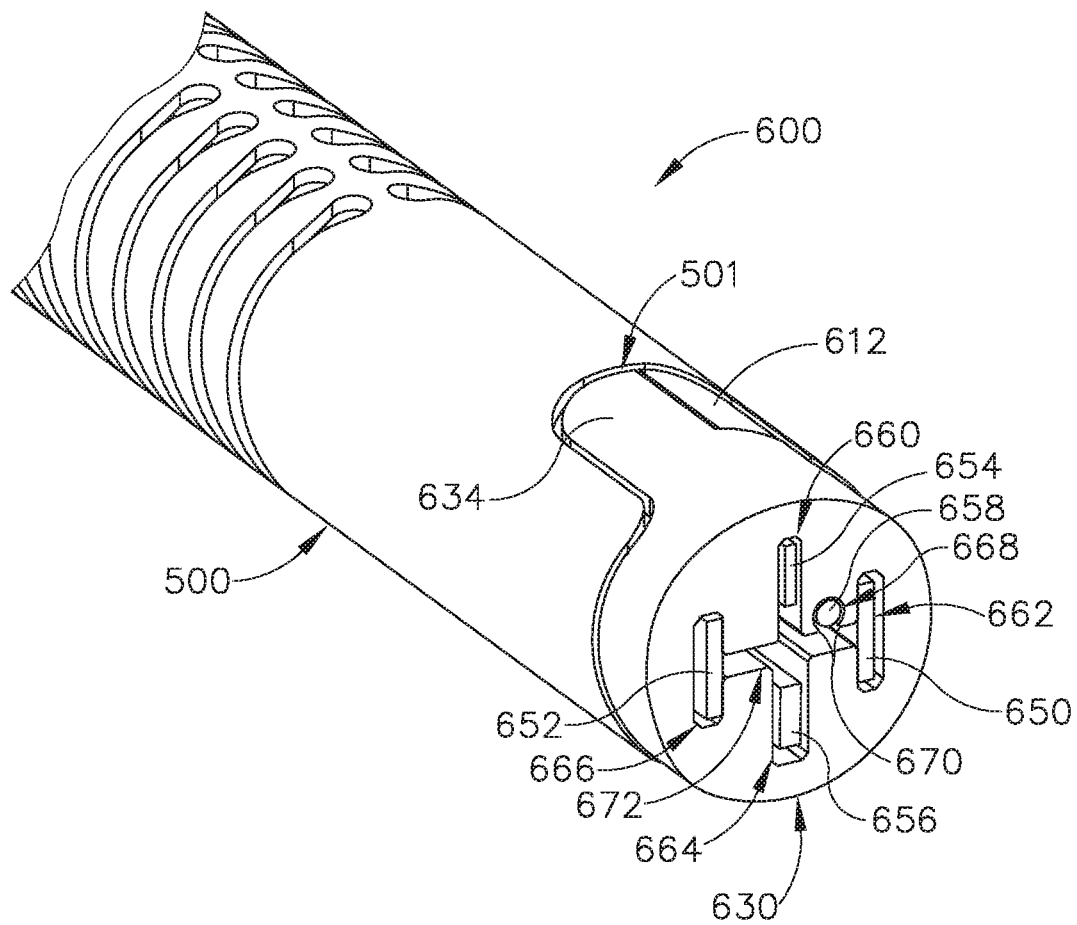
FIG. 30 depicts a perspective cross-sectional view of the articulation assembly of FIG. 23, taken along line 30-30 of FIG. 23.

With frame members (610, 630) joined together, proximal alignment feature portions (612, 634) cooperate to together define an alignment structure that is similar to distally extending alignment member (444). As best seen in FIGS. 23 and 30, this alignment structure is configured to fit in a proximally presented notch (501) of outer sleeve (500), thereby providing alignment between frame members (610, 630) and outer sleeve (500) and preventing frame members (610, 630) from rotating relative to outer sleeve (500). The positioning of alignment feature portions (612, 634) in notch (501) may further prevent the proximal ends of frame members (610, 630) from laterally separating from each other.

Narrowed regions (614, 636) are configured to allow frame members (610, 630) to flex laterally along only one plane (i.e., along a plane that is perpendicular to the plane along which upper jaw (412) pivots relative to lower jaw (414)). Ribs (618, 640) are configured to receive and support corresponding band portions (650, 652), and which are configured and operable like band portions (308, 426, 428) to drive articulation of articulation assembly (600). As shown in FIG. 23, distally presented surface (638) of second frame member (630) is located at a first longitudinal position ($LP_1$), such that second frame member (630) becomes flexible at first longitudinal position ($LP_1$). While not shown in FIG. 23, distally presented surface (616) of first frame member (610) is also located at first longitudinal position ($LP_1$), such that first frame member (610) becomes flexible at first longitudinal position ($LP_1$). The proximal-most slit (512) of outer sleeve (500) is located at a second longitudinal position ($LP_2$), such that outer sleeve (500) becomes flexible at second longitudinal position ($LP_2$). These longitudinal positions ($LP_1$, $LP_2$) are longitudinally separated by a distance (d). This separation may reduce stress in frame members (610, 630) and/or outer sleeve (500) during articulation of articulation section (600). This may be due to the highest strain occurring at the initial bending point of frame members (610, 630) and outer sleeve (500). Having these initial bending points located at different longitudinal positions ($LP_1$, $LP_2$) may reduce the strains at each of these points.

Figure 27:
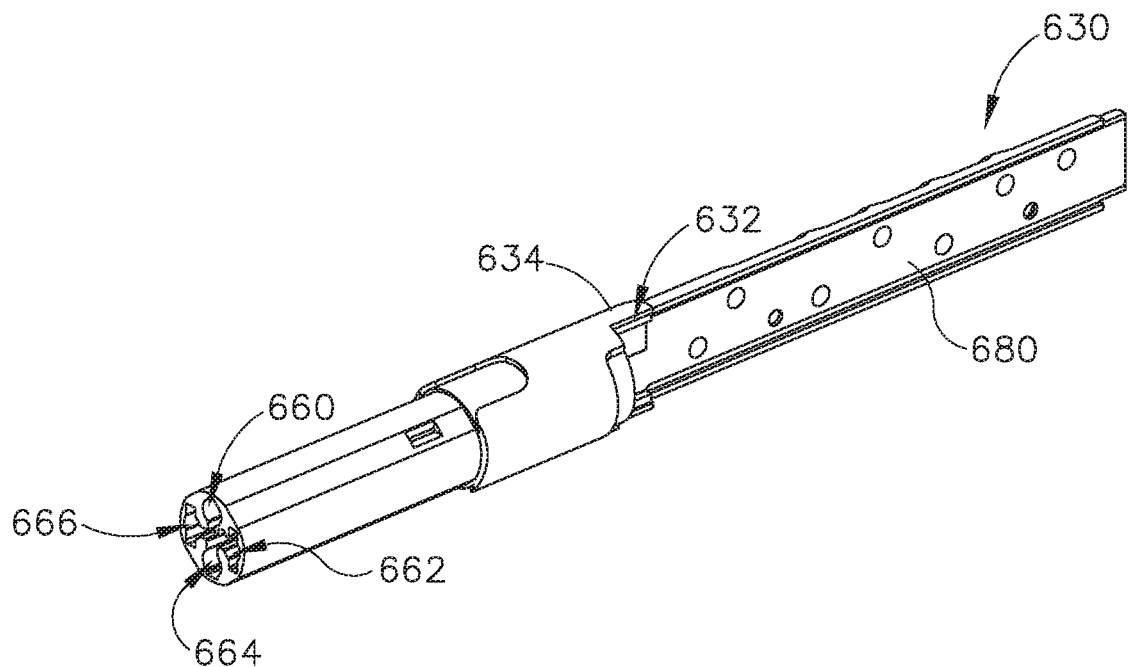
FIG. 27 depicts another perspective view of the frame member of FIG. 26.
Figure 29:
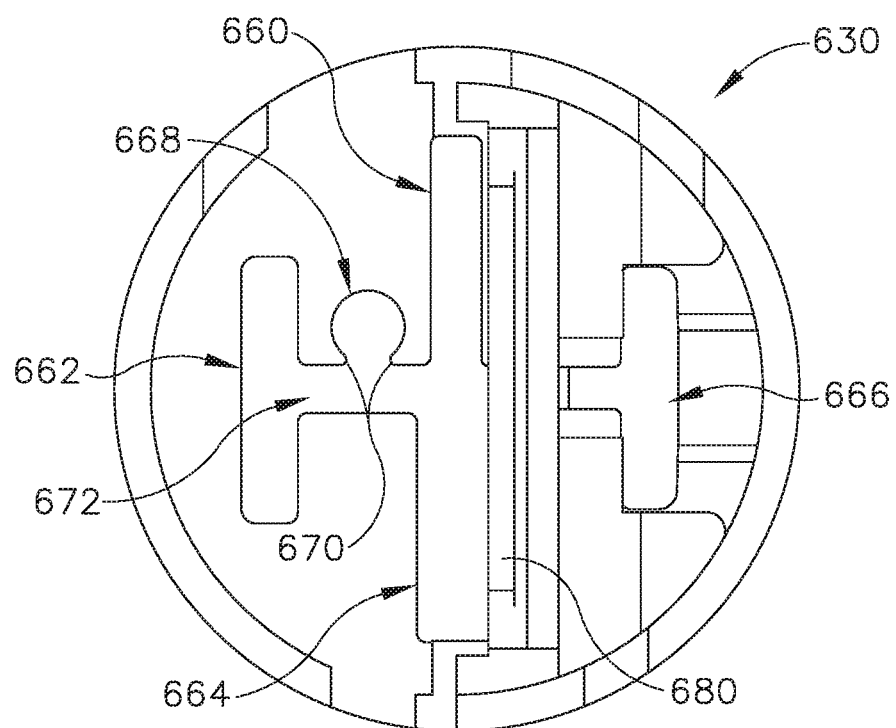
FIG. 29 depicts a distal end view of the frame member of FIG. 26.

As shown in FIGS. 27 and 29, a metal plate (680) is secured along a portion of the length of second frame member (630). Metal plate (680) is configured to provide additional reinforcement along a vertical plane (i.e., the plane along which upper jaw (412) pivots relative to lower jaw (414)). Such reinforcement may be particularly beneficial when upper jaw (412) is actuated to firmly compress tissue against lower jaw (414). While metal plate (680) provides reinforcement along a vertical plane, metal plate (680) does not prevent articulation section (600) from bending laterally (i.e., along a plane that is perpendicular to the plane along which upper jaw (412) pivots relative to lower jaw (414)). Other suitable structures may be used in addition to or in lieu of metal plate (680). Moreover, metal plate (680) may simply be omitted in some versions.

As shown in FIGS. 26-30, second frame member (630) further includes a set of channels (660, 662, 664, 666, 668). Channel (660) is configured to slidably receive knife member (654), which is configured and operable like knife member (360) described above. Channel (662) is configured to slidably receive band portion (650). Channel (664) is configured to slidably receive band portion (656) of a jaw closure connector (not shown), which is configured and operable like band portion (338) of jaw closure connector (330) described above. Channel (666) is configured to slidably receive band portion (652). Channel (668) is configured to slidably receive electrical wire (658), which is configured and operable like electrical wire (15) described above. By way of example only electrical wire (658) may comprise a wire formed of sterling silver, gold, copper, and/or any other suitable material or combination of materials.

Figure 28:
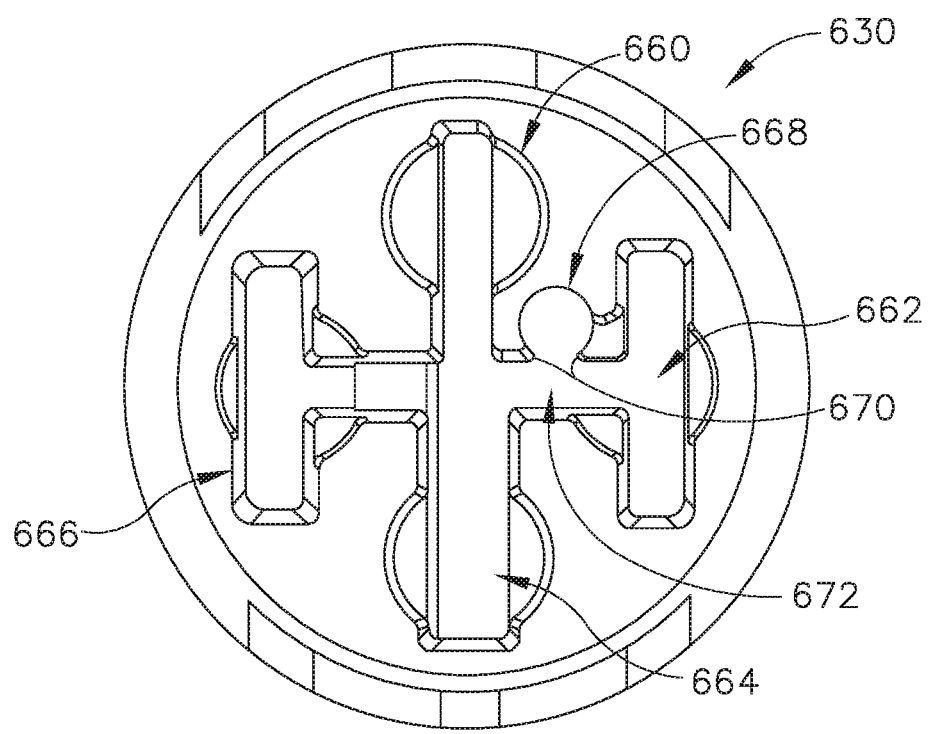
FIG. 28 depicts a proximal end view of the frame member of FIG. 26.

As best seen in FIGS. 28-30, channel (668) is defined in part by a pair of stubs (670), such that channel (668) has a configuration similar to an "Ω" symbol. These stubs (670) provide a path for communication between channel (668) and a channel (672) that extends laterally between channels (662, 666); yet stubs (670) are configured to prevent electrical wire (658) from falling into channel (672). In other words, stubs (670) contain electrical wire (658) in channel (668). By preventing electrical wire (658) from falling in channel (672), stubs (670) prevent electrical wire (658) from getting tangled with or otherwise causing interference with the various components (650, 652, 654, 656) that translate within frame member (630).

As shown in FIGS. 3-5, the various components (312, 330, 360) that translate longitudinally to provide articulation, jaw closure, and tissue cutting all transition from having circular cross-sectional profiles to having flat, rectangular cross-sectional profiles. In the present example, the analogous translating components (650, 652, 654, 656) have the same transition from circular cross-sectional profiles to flat, rectangular cross-sectional profiles. To accommodate these varying cross-sectional profiles, the proximal ends of channels (660, 662, 664, 666) have circular cross-sectional profiles (as best seen in FIG. 28); while the distal ends of channels (660, 662, 664, 666) have flat, rectangular cross-sectional profiles (as best seen in FIG. 29).

V. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly defines a longitudinal axis; (c) an end effector located distally relative to the shaft assembly; and (d) an articulation section longitudinally interposed between a distal end of the shaft assembly and a proximal end of the end effector, wherein the articulation section is configured to flex to thereby provide deflection of the end effector away from the longitudinal axis of the shaft assembly, wherein the articulation sections comprises: (i) a first frame member having a distal end and a proximal end, (ii) a second frame member having a distal end and a proximal end, wherein the proximal end of the second frame member is proximal to the proximal end of the first frame member, and (iii) a sleeve disposed about the first and second frame members.

Example 2

The apparatus of Example 1, wherein the distal ends of the first and second frame members are located at the same longitudinal position.

Example 3

The apparatus of any one or more of Examples 1 through 2, wherein the shaft assembly comprises an electrically conductive external sheath, wherein the external sheath has a distal end, wherein the distal end of the external sheath abuts the proximal end of the second frame member.

Example 4

The apparatus of Example 3, wherein the second frame member is formed of an electrically non-conductive material.

Example 5

The apparatus of Example 4, further comprising at least one electrically conductive component slidably disposed within the second frame member, wherein the second frame member is configured to electrically insulate the at least one electrically conductive component relative to the external sheath.

Example 6

The apparatus of Example 5, wherein the end effector comprises: (i) a first jaw, and (ii) a second jaw, wherein the first jaw is configured to pivot toward and away from the second jaw, wherein the at least one electrically conductive component comprises a jaw actuator, wherein the jaw actuator is configured to translate to thereby pivot the first jaw relative to the second jaw.

Example 7

The apparatus of any one or more of Examples 5 through 6, wherein the end effector comprises a translating blade member, wherein the at least one electrically conductive component comprises a blade actuator, wherein the blade actuator is configured to translate to thereby translate the blade member.

Example 8

The apparatus of any one or more of Examples 5 through 7, wherein the at least one electrically conductive component comprises an articulation band, wherein the articulation band is configured to translate to thereby cause the articulation section to flex to thereby deflect the end effector away from the longitudinal axis of the shaft assembly.

Example 9

The apparatus of any one or more of Examples 5 through 8, wherein the end effector comprises an electrode, wherein the at least one electrically conductive component comprises a wire in electrical communication with the electrode.

Example 10

The apparatus of any one or more of Examples 1 through 9, wherein the first frame member further comprises a first proximal alignment feature portion, wherein the second frame member further comprises a second proximal alignment feature portion, wherein the first and second proximal alignment feature portions are configured to cooperate to define a proximal alignment feature, wherein the sleeve has a proximal end defining a notch, wherein the proximal alignment feature is positioned in the notch.

Example 11

The apparatus of any one or more of Examples 1 through 10, wherein the articulation section further comprises a plate, wherein the plate is secured to a laterally presented side of the second frame member.

Example 12

The apparatus of Example 11, wherein the plate comprises metal.

Example 13

The apparatus of any one or more of Examples 11 through 12, wherein the plate is laterally interposed between the first and second frame members.

Example 14

The apparatus of any one or more of Examples 1 through 13, wherein the second frame member further comprises a first passageway and a second passageway, wherein the first passageway is configured to receive a translating actuator, wherein the second passageway is configured to receive a wire, wherein the second frame member is configured to retain the wire in the second passageway to thereby prevent engagement between the translating actuator and the wire.

Example 15

The apparatus of any one or more of Examples 1 through 14, wherein the first and second frame members are both configured to flex at a first proximal-most longitudinal position of flexure, wherein the sleeve is configured to flex at a second proximal-most longitudinal position of flexure, wherein the first and second proximal-most longitudinal positions of flexure are longitudinally offset from each other.

Example 16

The apparatus of Example 15, wherein the first proximal-most longitudinal position of flexure is proximal to the second proximal-most longitudinal position of flexure.

Example 17

The apparatus of any one or more of Examples 1 through 16, wherein the sleeve comprises a plurality of slits, wherein the slits are longitudinally spaced apart from each other along a flexible region of the sleeve.

Example 18

The apparatus of Example 17, wherein each slit angularly) terminates in widened lobes.

Example 19

An apparatus comprising: (a) a body; (b) a shaft assembly extending distally from the body, wherein the shaft assembly defines a longitudinal axis; (c) an end effector located distally relative to the shaft assembly; and (d) an articulation section longitudinally interposed between a distal end of the shaft assembly and a proximal end of the end effector, wherein the articulation section is configured to flex to thereby provide deflection of the end effector away from the longitudinal axis of the shaft assembly, wherein the articulation sections comprises: (i) a flexible frame assembly, and (ii) a sleeve disposed about the flexible frame assembly, wherein the sleeve comprises: (A) a rigid proximal portion having a circular cross-sectional profile, (B) a rigid distal portion having a circular cross-sectional profile, and (C) a flexible portion positioned between the proximal and distal portion, wherein the flexible portion includes a series of slits longitudinally spaced apart from each other, wherein the slits terminate in spines, wherein the spines are positioned at first and second angular positions about the circumference of the flexible portion, wherein the flexible portion further includes concave regions defined at third and fourth angular positions about the circumference of the flexible portion, wherein the first and second angular positions are angularly offset from each other by 180 degrees, wherein the third and fourth angular positions are angularly offset from each other by 180 degrees.

Example 20

An apparatus comprising: (a) a body; (b) a shaft assembly extending distally from the body, wherein the shaft assembly defines a longitudinal axis; (c) an end effector located distally relative to the shaft assembly; (d) an articulation section longitudinally interposed between a distal end of the shaft assembly and a proximal end of the end effector, wherein the articulation section is configured to flex to thereby provide deflection of the end effector away from the longitudinal axis of the shaft assembly, wherein the articulation sections comprises: (i) a first frame member having a distal end and a proximal end, wherein the proximal end of the first frame member presents a first cam surface, (ii) a second frame member having a distal end and a proximal end, wherein the proximal end of the second frame member presents a second cam surface, and (iii) a sleeve disposed about the first and second frame members; and (e) an adapter interposed between the shaft assembly and the articulation section, wherein the adapter has a distal end presenting third and fourth cam surfaces, wherein the third cam surface is configured to engage the first cam surface and thereby drive the first frame member outwardly into engagement with the sleeve, wherein the fourth cam surface is configured to engage the second cam surface and thereby drive the second frame member outwardly into engagement with the sleeve.

VI. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein. For instance, the teachings herein may be readily combined with various teachings in U.S. Pat. No. 9,526,565, the disclosure of which is incorporated by reference herein; U.S. Pat. No. 9,492,224, the disclosure of which is incorporated by reference herein; and/or U.S. Pub. No. 2016/0100882, issued as U.S. Pat. No. 10,292,758 on May 21, 2019, the disclosure of which is incorporated by reference herein. Various suitable ways in which such teachings may be combined will be apparent to those of ordinary skill in the art.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Filing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued as U.S. Pat. No. 8,408,439 on Apr. 2, 2013; and U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) a body;
    (b) a shaft assembly extending distally from the body, wherein the shaft assembly defines a longitudinal axis;
    (c) an end effector located distally relative to the shaft assembly; and
    (d) an articulation section longitudinally interposed between a distal end of the shaft assembly and a proximal end of the end effector, wherein the articulation section is configured to flex to thereby provide deflection of the end effector away from the longitudinal axis of the shaft assembly, wherein the articulation section comprises:
        (i) a first frame member comprising a distal end, a proximal end, and a first alignment feature,
        (ii) a second frame member comprising a distal end, a proximal end, and a second alignment feature, wherein the proximal end of the second frame member is proximal to the proximal end of the first frame member, and
        (iii) a sleeve disposed about the first and second frame members, wherein the sleeve comprises a complementary alignment feature configured to directly engage both the first alignment feature and the second alignment feature to rotationally align the sleeve with the first and second frame members via the first alignment feature and the second alignment feature; and
    (e) an articulation drive assembly configured to actuate relative to the shaft assembly in order to drive the flexing of the articulation section, wherein the articulation drive assembly comprises:
        (i) a first elongated element slidably contained within a channel of the first frame member, and
        (ii) a second elongated element slidably contained within a channel of the second frame member.

2. The apparatus of claim 1, wherein the distal ends of the first and second frame members are located at the same longitudinal position.

3. The apparatus of claim 1, wherein the shaft assembly comprises an electrically conductive external sheath, wherein the electrically conductive external sheath has a distal end, wherein the distal end of the electrically conductive external sheath abuts the proximal end of the second frame member.

4. The apparatus of claim 3, wherein the second frame member is formed of an electrically non-conductive material.

5. The apparatus of claim 4, further comprising at least one electrically conductive component slidably disposed within the second frame member, wherein the second frame member is configured to electrically insulate the at least one electrically conductive component relative to the electrically conductive external sheath.

6. The apparatus of claim 5, wherein the end effector comprises an electrode, wherein the at least one electrically conductive component comprises a wire in electrical communication with the electrode.

7. The apparatus of claim 4, wherein the second elongated element comprises an electrically conductive component configured to translate to thereby cause the articulation section to flex to thereby deflect the end effector away from the longitudinal axis of the shaft assembly, wherein the second frame member is configured to electrically insulate the electrically conductive component relative to the electrically conductive external sheath.

8. The apparatus of claim 1, wherein the complementary alignment feature of the sleeve comprises a notch, wherein the first alignment feature and the second alignment feature are positioned in the notch.

9. The apparatus of claim 1, wherein the articulation section further comprises a plate, wherein the plate is secured to a laterally presented side of the second frame member.

10. The apparatus of claim 9, wherein the plate comprises metal.

11. The apparatus of claim 9, wherein the plate is laterally interposed between the first and second frame members.

12. The apparatus of claim 1, wherein the second frame member further comprises a first passageway and a second passageway, wherein the first passageway is configured to receive a knife member, wherein the second passageway is configured to receive a wire, wherein the second frame member is configured to retain the wire in the second passageway to thereby prevent engagement between the knife member and the wire.

13. The apparatus of claim 1, wherein the first and second frame members are both configured to flex at a first proximal-most longitudinal position of flexure, wherein the sleeve is configured to flex at a second proximal-most longitudinal position of flexure, wherein the first and second proximal-most longitudinal positions of flexure are longitudinally offset from each other.

14. The apparatus of claim 13, wherein the first proximal-most longitudinal position of flexure is proximal to the second proximal-most longitudinal position of flexure.

15. The apparatus of claim 1, wherein the sleeve comprises a plurality of slits, wherein the slits are longitudinally spaced apart from each other along a flexible region of the sleeve.

16. The apparatus of claim 15, wherein each slit angularly terminates in widened lobes.

17. An apparatus comprising:
(a) a body;
(b) a shaft assembly extending distally from the body, wherein the shaft assembly defines a longitudinal axis;
(c) an end effector located distally relative to the shaft assembly; and
(d) an articulation section longitudinally interposed between a distal end of the shaft assembly and a proximal end of the end effector, wherein the articulation section is configured to flex to thereby provide deflection of the end effector away from the longitudinal axis of the shaft assembly, wherein the articulation section comprises:
(i) a first frame member having a distal end and a proximal end,
(ii) a second frame member having a distal end and a proximal end, wherein the proximal end of the second frame member is proximal to the proximal end of the first frame member, wherein the first and second frame members are both configured to flex at a first proximal-most longitudinal position of flexure,
(iii) a sleeve disposed about the first and second frame members, wherein the sleeve is configured to flex at a second proximal-most longitudinal position of flexure, wherein the first and second proximal-most longitudinal positions of flexure are longitudinally offset from each other, and
(iv) an articulation drive assembly configured to actuate relative to the shaft assembly in order to drive the flexing of the articulation section, wherein the articulation drive assembly comprises:
(A) a first actuating body slidably confined within the first frame member, and
(B) a second actuating body slidably confined within the second frame member.

18. An apparatus comprising:
(a) a body;
(b) a shaft assembly extending distally from the body, wherein the shaft assembly defines a longitudinal axis;
(c) an end effector located distally relative to the shaft assembly; and
(d) an articulation section longitudinally interposed between a distal end of the shaft assembly and a proximal end of the end effector, wherein the articulation section is configured to flex to thereby provide deflection of the end effector away from the longitudinal axis of the shaft assembly, wherein the articulation section comprises:
(i) a first frame member having a distal end and a proximal end,
(ii) a second frame member having a distal end and a proximal end, wherein the proximal end of the second frame member is proximal to the proximal end of the first frame member, wherein the second frame member comprises a laterally presented side that faces an interior of the first frame member,
(iii) a sleeve disposed about the first and second frame members,
(iv) an articulation drive assembly configured to actuate relative to the shaft assembly in order to drive the flexing of the articulation section, wherein the articulation drive assembly comprises:
(A) a first sliding body slidably contained within a channel of the first frame member, and
(B) a second sliding body slidably contained within a channel of the second frame member, and
(v) a plate secured to the laterally presented side of the second frame member such that the plate is between the first frame member and the second frame member.

* * * * *